United States Patent
Ganesan et al.

(10) Patent No.: US 12,064,262 B2
(45) Date of Patent: *Aug. 20, 2024

(54) PHYSIOLOGICAL SENSING TEXTILE APPARATUS

(71) Applicant: University of Massachusetts, Boston, MA (US)

(72) Inventors: Deepak Ganesan, Amherst, MA (US); Trisha L. Andrew, Hadley, MA (US); Ali Kiaghadi, Amherst, MA (US); Seyedeh Zohreh Homayounfar, Amherst, MA (US); Jeremy Gummeson, Belchertown, MA (US)

(73) Assignee: University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/818,158

(22) Filed: Aug. 8, 2022

(65) Prior Publication Data
US 2022/0386957 A1     Dec. 8, 2022

Related U.S. Application Data

(63) Continuation of application No. 17/593,940, filed as application No. PCT/US2020/025943 on Mar. 31, 2020, now Pat. No. 11,445,976.

(Continued)

(51) Int. Cl.
*B32B 7/025* (2019.01)
*A41D 1/00* (2018.01)
(Continued)

(52) U.S. Cl.
CPC ............ *A61B 5/6804* (2013.01); *A41D 1/005* (2013.01); *A41D 31/04* (2019.02); *A61B 5/1102* (2013.01);
(Continued)

(58) Field of Classification Search
CPC ... A61B 5/6804; A61B 5/1102; A61B 5/1116; A61B 5/6823; A61B 2562/0247;
(Continued)

(56) References Cited

U.S. PATENT DOCUMENTS

2005/0279696 A1*  12/2005  Bahm .................. B01J 20/3268
                                                    210/446
2016/0278709 A1*  9/2016  Ridao Granado ...... G01L 1/205
(Continued)

FOREIGN PATENT DOCUMENTS

WO    WO-2015014950 A1    2/2015
WO    WO-2020205853 A1    10/2020

OTHER PUBLICATIONS

Zhang, et al., "Rugged Textile Electrodes for Wearable Devices Obtained by Vapor Coating Off-the-Shelf, Plain-Woven Fabrics." Adv. Funct. Mater. 2017, 27, 1700415. (Year: 2017).*

(Continued)

*Primary Examiner* — Matthew D Matzek
(74) *Attorney, Agent, or Firm* — Schwegman Lundberg & Woessner, P.A.

(57) ABSTRACT

A garment system comprises a garment substrate formed from one or more textile-based sheets, a distributed array of a plurality of resistive pressure sensors coupled to the garment substrate at a set of first specified locations. Each of the plurality of resistive sensors comprises a pair of first textile-based outer layers each having an electrical resistance of no more than 100 ohms and a textile-based inner layer sandwiched between the pair of first textile-based outer layers having an electrical resistance of at least 1 mega-ohm. The system also includes electronics configured to process signals from the distributed array of resistive pressure sensors to determine one or more physiological properties of a wearer of the garment substrate.

19 Claims, 20 Drawing Sheets

Related U.S. Application Data

(60) Provisional application No. 62/827,240, filed on Apr. 1, 2019.

(51) Int. Cl.
| | | |
|---|---|---|
| *A41D 31/04* | (2019.01) | |
| *A61B 5/00* | (2006.01) | |
| *A61B 5/11* | (2006.01) | |
| *B32B 3/08* | (2006.01) | |
| *B32B 5/02* | (2006.01) | |
| *B32B 5/26* | (2006.01) | |

(52) U.S. Cl.
CPC .......... *A61B 5/1116* (2013.01); *A61B 5/6823* (2013.01); *B32B 3/08* (2013.01); *B32B 5/024* (2013.01); *B32B 5/26* (2013.01); *B32B 7/025* (2019.01); *A61B 2562/0247* (2013.01); *B32B 2250/20* (2013.01); *B32B 2255/02* (2013.01); *B32B 2255/205* (2013.01); *B32B 2255/26* (2013.01); *B32B 2262/0261* (2013.01); *B32B 2262/062* (2013.01); *B32B 2307/202* (2013.01); *B32B 2307/204* (2013.01); *B32B 2307/206* (2013.01); *B32B 2307/73* (2013.01); *B32B 2437/00* (2013.01)

(58) Field of Classification Search
CPC .. B32B 3/08; B32B 5/024; B32B 5/26; B32B 7/025; B32B 2250/20; B32B 2255/02; B32B 2255/205; B32B 2255/26; B32B 2262/0261; B32B 2262/062; B32B 2307/202; B32B 2307/204; B32B 2307/206; B32B 2307/73; B32B 2437/00; A41D 1/005; A41D 31/04
USPC .................................. 600/372–397; 442/100
See application file for complete search history.

(56) References Cited

U.S. PATENT DOCUMENTS

| | | | |
|---|---|---|---|
| 2017/0196513 A1* | 7/2017 | Longinotti-Buitoni | ...................... A61B 5/7405 |
| 2018/0184735 A1 | 7/2018 | Longinotti-Buitoni et al. | |
| 2018/0343930 A1 | 12/2018 | Alipour et al. | |
| 2018/0356303 A1* | 12/2018 | Li | ........................... G06F 3/044 |
| 2020/0337569 A1* | 10/2020 | Tauban | ................... B32B 27/36 |
| 2022/0087607 A1 | 3/2022 | Ganesan et al. | |

OTHER PUBLICATIONS

"U.S. Appl. No. 17/593,940 Preliminary Amendment Filed with Application", 7 pgs.
"U.S. Appl. No. 17/593,940, Non Final Office Action mailed Feb. 3, 2022".
"U.S. Appl. No. 17/593,940, Notice of Allowance mailed May 26, 2022", 8 pgs.
"U.S. Appl. No. 17/593,940, Response filed May 3, 2022 to Non Final Office Action mailed Feb. 3, 2022", 10 pgs.
"International Application Serial No. PCT/US2020/025943, International Preliminary Report on Patentability mailed Oct. 14, 2021", 7 pgs.
"International Application Serial No. PCT/US2020/025943, International Search Report mailed Jun. 18, 2020", 2 pgs.
"International Application Serial No. PCT/US2020/025943, Written Opinion mailed Jun. 18, 2020", 5 pgs.
"Murata Ultra Low Noise MEMS Based Ballistocardiogram", muRata, [Online] Retrieved from the Internet: <URL: https://web.archive.org/web/20160629115605/http://www.mouser.com/new/Murata/murata-bcg-mems-sensor/>, (captured Jun. 29, 2016), 2 pgs.
"Sleep position gives personality clue", BBC News, [Online] Retrieved from the Internet: <URL: http://news.bbc.co.uk/2/hi/health/3112170.stm>, (Sep. 16, 2003), 3 pgs.
Alametsa, J, et al., "The potential of EMFi sensors in heart activity monitoring", 2nd Open ECG Workshop Integration of the ECG into the EHR and Interoperability of ECG Device Systems, Berlin, Germany. Citeseer,, (2004), 83-85.
Andreoni, Giuseppe, et al., "Defining Requirements and Related Methods for Designing Sensorized Garments", Sensors, 16(6), (2016), 16 pgs.
Bicen, A. Ozan, et al., "Template-Based Statistical Modeling and Synthesis for Noise Analysis of Ballistocardiogram Signals: A Cycle-Averaged Approach", IEEE J Biomed Health Inform. 23(4), (Jul. 2019), 26 pages.
Brosschot, Jos F, et al., "Daily worry is related to low heart rate variability during waking and the subsequent nocturnal sleep period", International Journal of Psychophysiology, 63(1), (2007), 39-47.
Dong, Zhao, et al., "Frequency Network Analysis of Heart Rate Variability for Obstructive Apnea Patient Detection", IEEE Journal of Biomedical and Health Informatics, 22(6), (2018), 1895-1905.
Dunne, Lucy E, et al., "Design and Evaluation of a Wearable Optical Sensor for Monitoring Seated Spinal Posture", 2006 10th IEEE International Symposium on Wearable Computers, (Oct. 2006), 65-68.
Elad, Michael, et al., "Image Denoising Via Sparse and Redundant Representations Over Learned Dictionaries", IEEE Transactions on Image Processing, 15(12), (Dec. 2006), 3736-3745.
Elad, Michael, "Sparse & Redundant Representations and Their Applications in Signal and Image Processing", Springer Publishing Company, Incorporated, 1st ed., (2010), 101 pages.
Estrada, Jheanel E, et al., "Real-Time Human Sitting Posture Detection Using Mobile Devices", 2016 IEEE Region 10 Symposium (TENSYMP), Bali, Indonesia, (2016), 5 pgs.
Fathi, Azin, et al., "Detection of spine curvature using wireless sensors", Journal of King Saud University—Science, 29(4), (2017), 553-560.
Gomez-Clapers, Joan, et al., "Towards the standardization of ballistocardiography systems for J-peak timing measurement", Measurement, 58, (2014), 310-316.
Hall, M, et al., "Acute Stress Affects Heart Rate Variability During Sleep", Psychosomatic medicine, 66(1), (2004), pp. 56-62.
Hua, Nan, et al., "Just-in-time Sampling and Pre-filtering for Wearable Physiological Sensors: Going from Days to Weeks of Operation on a Single Charge", Wireless Health, ACM, (2010), 54-63.
Hwang, Su Hwan, et al., "Nocturnal Awakening and Sleep Efficiency Estimation Using Unobtrusively Measured Ballistocardiogram", IEEE Transactions on Biomedical Engineering, 61(1), (Jan. 2014), 131-138.
Jia, Z, "Monitoring a person's heart rate and respiratory rate on a shared bed using geophones", SenSys 17 Delft Netherlands, (Nov. 2017), 14 pages.
Jia, Zhenhua, "HB-Phone: a Bed-Mounted Geophone-Based Heartbeat Monitoring System", Proceedings of the 15th International Conference on Information Processing in Sensor Networks, IEEE Press, (2016), 12 pgs.
Kiaghadi, et al., "Phyjama: Physiological Sensing via Fiber-enhanced Pyjamas", Association for Computing Machinery, vol. 3, No. 3, Article 89, (Sep. 2019), 1-29.
Kiaghadi, Ali, et al., "Fabric as a Sensor: Towards Unobtrusive Sensing of Human Behavior with Triboelectric Textiles", Proceedings of the 16th ACM Conference on Embedded Networked Sensor Systems, SenSys T8, New York, NY, USA, ACM, (2018), 199-210.
Kim, Chan-Sei, et al., "Ballistocardiogram as Proximal Timing Reference for Pulse Transit Time Measurement: Potential for Cuffless Blood Pressure Monitoring", IEEE Trans Biomed Eng., 62(11), (2015), 2657-2664.
Lorussi, Federico, et al., "Wearable, Redundant Fabric-Based Sensor Arrays for Reconstruction of Body Segment Posture", IEEE Sensors Journal, 4(6), (2004), 807-818.
Mairal, Julien, et al., "Online Dictionary for Sparse Coding", Proceedings of the 26th Annual International Conference on Machine Learning, (2009), 689-696.

(56) References Cited

OTHER PUBLICATIONS

Mairal, Julien, et al., "Online Learning for Matrix Factorization and Sparse Coding", arXiv:0908.0050v2; J. Mach. Learn. Res., 11:19-60, (2010), 45 pgs.

Olhausen, Bruno A, et al., "Sparse Coding with an Overcomplete Basis Set: A Strategy Employed by V1?", Vision Res., 37(23), (1997), 3311-3325.

Paradiso, Rita, et al., "A Wearable Health Care System Based on Knitted Integrated Sensors", IEEE Transactions on Information Technology in Biomedicine, 9(3), (Sep. 2005), 337-344.

Roche, Frederic, et al., "Screening of Obstructive Sleep Apnea Syndrome by Heart Rate Variability Analysis", Circulation, 100(13): 1411-1415, (1999), 17 pgs.

Sardini, Emilio, et al., "Wireless Wearable T-Shirt for Posture Monitoring During Rehabilitation Exercises", IEEE Transactions on Instrumentation and Measurement, 64(2), (Feb. 2015), 439-448.

Shao, Dangdang, et al., "Simultaneous Monitoring of Ballistocardiogram and Photoplethysmogram Using Camera", IEE Tran Biomed Biomed Eng 64 5, (May 2017), pp. 1003-1010.

Shu, Yi, et al., "A Pressure Sensing System for Heart Rate Monitoring with Polymer-Based Pressure Sensors and an Anti-Interference Post Processing Circuit", Sensors, 15(2), (2015), 3224-3235.

Stein, Phyllis K, et al., "Heart rate variability: A measure of cardiac autonomic tone", American heart journal, 127(5), (1994), 1376-1381.

Vanoli, E., et al., "Heart rate variability during specific sleep stages: a comparison of healthy subjects with patients after myocardial infarction", Circulation, 91(7), (1995), 1918-1922.

Vesterinen, V., et al., "Heart rate variability in prediction of individual adaptation to endurance training in recreational endurance runners", Scandinavian journal of medicine & science in sports. 23(2), (2013), 171-180.

Wang, Lin Wang, et al., "Progress in triboelectric nanogenertors as new energy technology and self-powered sensorst", Energy & Environmental Science, 8(8), (2015), 2250-2282.

Wanwong, Sompit, et al., "Wash-stable, oxidation resistant conductive cotton electrodes for wearable electronics", RSC Adv., 9:9198-9203,, (2019), 6 pgs.

Wong, Wai Yin, et al., "Smart garment for trunk posture monitoring: A preliminary study", Scoliosis, 3(1):7, (May 2008), 9 pgs.

Xiao, M., et al., "Sleep stages classification based on heart rate variability and random forest. Biomedical Signal Processing and Control", Biomedical Signal Processing and Control, 8(6), (2013), pp. 624-633.

Yang, Jianchaoi, et al., "Linear Spatial Pyramid Matching Using Sparse Coding for Image Classification", 2009 IEEE Conference on Computer Vision and Pattern Recognition, (Jun. 2009), 1794-1801.

Zhang, "Rugged Textile Electrodes for Wearable Devices Obtained by Vapor Coating Off-the-Shelf, Plain-Woven Fabrics,", Advanced Functional Materials,, 27, 1700415., (2017).

Zhang, Lushuai, et al., "All-Textile Triboelectric Generator Compatible with Traditional Textile Process", Advanced Materials Technologies, I(9):1600147, (2016), 8 pgs.

U.S. Appl. No. 17/593,940, filed Sep. 28, 2021, Physiological Sensing Textile Apparatus.

\* cited by examiner

PHYSIOLOGICAL SENSING TEXTILE APPARATUS

CROSS-REFERENCE TO RELATED APPLICATION

This application is a continuation of U.S. patent application Ser. No. 17/593,940 entitled "PHYSIOLOGICAL SENSING TEXTILE APPARATUS," filed on Sep. 28, 2021, which is a U.S. National Stage filing under 35 U.S.C. § 371 of PCT Patent Application No. PCT/US2020/025943 entitled "PHYSIOLOGICAL SENSING TEXTILE APPARATUS," filed on Mar. 31, 2020, which claims the benefit of priority to U.S. Provisional Patent Application Ser. No. 62/827,240 entitled "PHYSIOLOGICAL SENSING TEXTILE APPARATUS," filed Apr. 1, 2019, the disclosures of which are incorporated herein in their entirety by reference.

STATEMENT OF GOVERNMENT SUPPORT

This invention was also made with government support under grant number 1763524 awarded by the National Science Foundation. The U.S. Government has certain rights in this invention.

BACKGROUND

Recently, there has been much interest in textile articles with the ability to monitor physiological conditions, such as heartrate or respiration. These so-called "smart textiles" often use flexible electronic components that are integrated with one or more textile layers to form a wearable textile article.

SUMMARY

The present disclosure describes a textile article with sensors integrated with one or more fabric or textile sheets. The sensors can measure one or more of respiration, heartbeat, and posture of the wearer, and is able to do so with a loose-fitting article of clothing rather than requiring a form-fitting garment, as has typically been required for existing smart textile articles that measure heart rate or respiration.

The present disclosure describes a textile-based garment system comprising a garment substrate formed from one or more textile-based sheets, one or more resistive pressure sensors coupled to the garment substrate at one or more first specified locations, one or more triboelectric sensors coupled to the garment at one or more second specified locations, and electronics configured to process signals from the one or more resistive pressure sensors and the one or more triboelectric sensors to determine one or more physiological properties of a wearer of the garment substrate. In an example, each of the one or more resistive pressure sensors comprises a pair of first textile-based outer layers each having an electrical resistance of no more than 100 ohms and a textile-based inner layer having an electrical resistance of at least 1 mega-ohm sandwiched between the pair of first textile-based outer. In an example, each of the one or more triboelectric sensors comprises a pair of second textile-based outer layers each having an electrical resistance of no more than 100 ohms and a textile-based triboelectric core sandwiched between the pair of second textile-based outer layers. In an example, the textile-based triboelectric core comprises a first textile-based dielectric layer and a second textile-based dielectric layer. In an example, the first textile-based dielectric layer comprises a first textile-based dielectric material that forms a positively-charged triboelectric surface and the second textile-based dielectric layer comprises a second textile-based dielectric material that forms a negatively-charged triboelectric surface. The positively-charged triboelectric surface of the first textile-based dielectric layer is adjacent and proximate to the negatively-charged triboelectric surface of the second textile-based dielectric layer.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

Figure 1A:
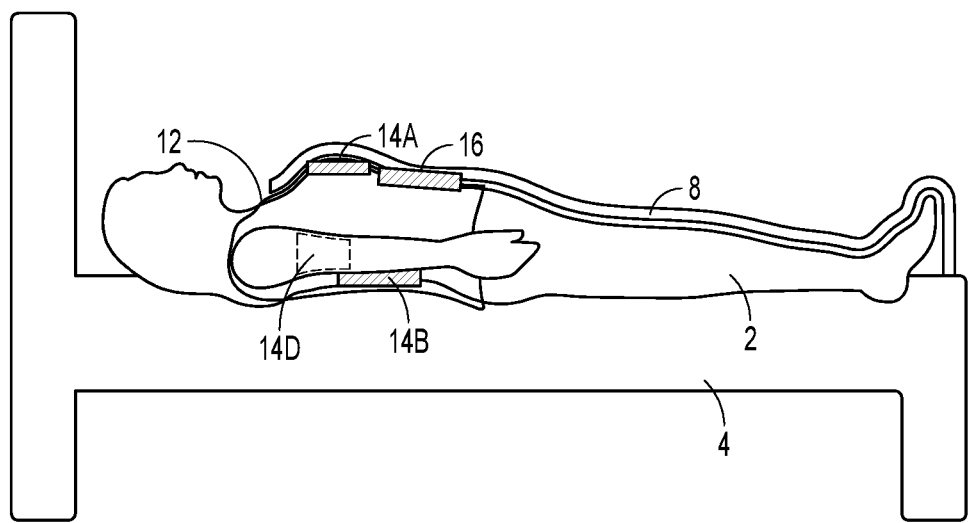
FIGS. 1A-1C are several views of an example textile-based system for sensing physiological conditions of a user.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The example embodiments may be combined, other embodiments may be utilized, or structural, and logical changes may be made without departing from the scope of the present invention. While the disclosed subject matter will be described in conjunction with the enumerated claims, it will be understood that the exemplified subject matter is not intended to limit the claims to the disclosed subject matter. The following detailed description is, therefore, not to be taken in a limiting sense, and the scope of the present invention is defined by the appended claims and their equivalents.

References in the specification to "one embodiment", "an embodiment," "an example embodiment," etc., indicate that the embodiment described can include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to affect such feature, structure, or characteristic in connection with other embodiments whether or not explicitly described.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y,'" unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. Unless indicated otherwise, the statement "at least one of" when referring to a listed group is used to mean one or any combination of two or more of the members of the group. For example, the statement "at least one of A, B, and C" can have the same meaning as "A; B; C; A and B; A and C; B and C; or A, B, and C," or the statement "at least one of D, E, F, and G" can have the same meaning as "D; E; F; G; D and E; D and F; D and G; E and F; E and G: F and G; D, E, and F; D, E, and G; D, F, and G; E, F, and G; or D, E, F, and G." A comma can be used as a delimiter or digit group separator to the left or right of a decimal mark; for example, "0.000,1'" is equivalent to "0.0001."

In the methods described herein, the acts can be carried out in any order without departing from the principles of the disclosed method, except when a temporal or operational sequence is explicitly recited. Furthermore, specified acts can be carried out concurrently unless explicit language recites that they be carried out separately. For example, a recited act of doing X and a recited act of doing Y can be conducted simultaneously within a single operation, and the resulting process will fall within the literal scope of the process. Recitation in a claim to the effect that first a step is performed, then several other steps are subsequently performed, shall be taken to mean that the first step is performed before or concurrently with any of the other steps, but the other steps can be performed in any suitable sequence, unless a sequence is further recited within the other steps. For example, claim elements that recite "Step A, Step B, Step C, Step D, and Step E" shall be construed to mean step A is carried out first (or concurrently with one or more of steps B, C, D, and E), step E is carried out last (or concurrently with one or more of steps A, B, C, and D) and, in some examples, steps B, C, and D can be carried out in any sequence between steps A and E, and that the sequence still falls within the literal scope of the claimed process. A given step or sub-set of steps may also be repeated.

The term "about" as used herein can allow for a degree of variability in a value or range, for example, within 10%, within 5%, within 1%, within 0.5%, within 0.1%, within 0.05%, within 0.01%, within 0.005%, or within 0.001% of a stated value or of a stated limit of a range, and includes the exact stated value or range.

The term "substantially" as used herein refers to a majority of, or mostly, such as at least about 50%, 60%, 70%, 80%, 90%, 95%, 96%, 97%, 98%, 99%, 99.5%, 99.9%, 99.99%, or at least about 99.999% or more, or 100%.

Electronically active textiles are potentially the future of portable, interactive devices. Textiles that use all-textile sensors and/or actuators that can be woven or stitched directly into a textile or garment are particularly exciting. While there are many smart textile-based garments already on the market, these generally use flexible electronic components that are integrated with textiles. However, enhancing textiles with electronics is challenging because of two reasons: a) it can change the aesthetics and tactile perception (or feel) of the textile, and b) the large and varied mechanical stresses to which textiles can be subjected can abrade or damage microelectronic components and electronic interconnects.

The present disclosure describes a textile garment system that uses a material that is likely already familiar to a user, such as cotton/silk thread and fabrics, and imperceptibly adapts it to enable sensing of physiological signals to yield natural fitting, comfortable, and less obtrusive smart clothing. Specifically, the present disclosure describes a garment shirt, and more specifically a pajama shirt, as a representative instance of a loosely-worn and comfortable article of clothing that many people wear at home and/or during sleep. A comfortable, loosely-worn sleepwear garment that can measure a variety of physiological signals continuously during sleep and other everyday situations can be a precursor to smart clothing that looks and feels more like normal clothing.

While the ability to instrument everyday textiles opens up exciting new possibilities, a challenge that has been faced is designing systems that measure physiological signals when the garment is loosely worn. Currently existing technologies for sensing respiratory and cardiac signals all rely on tightly worn bands or electrodes that are placed at specific locations on the skin. For example, a FITBIT fitness tracker or an APPLE WATCH on the wrist is robust to a small amount of motion noise but this is considerably less movement than what is encountered with a loose-fitting garment. Similarly, many of the ECG-sensing shirts on the market need a tight fit at several locations on the body to obtain a cardiac signal. In contrast, the garment systems and methods described herein enable physiological sensing with a wearable garment at the other end of the spectrum in terms of looseness, e.g., an extremely loose daily-use textile like a pajama that is designed with comfort in mind.

While looseness may appear to present a problem, even when a garment is considered "loose," there are several parts of the garment that are pressed against the body due to posture and/or contact with external surfaces. By carefully observing the different locations where a textile garment is naturally pressured, several categories or classes of pressured locations can be defined. Several of these naturally-pressured locations are shown in FIGS. 1A-1C, which shows the body 2 of a person in a supine lying posture (FIG. 1A), a sitting posture (FIG. 1B), and a standing posture (FIG. 1C).

Figure 1B:
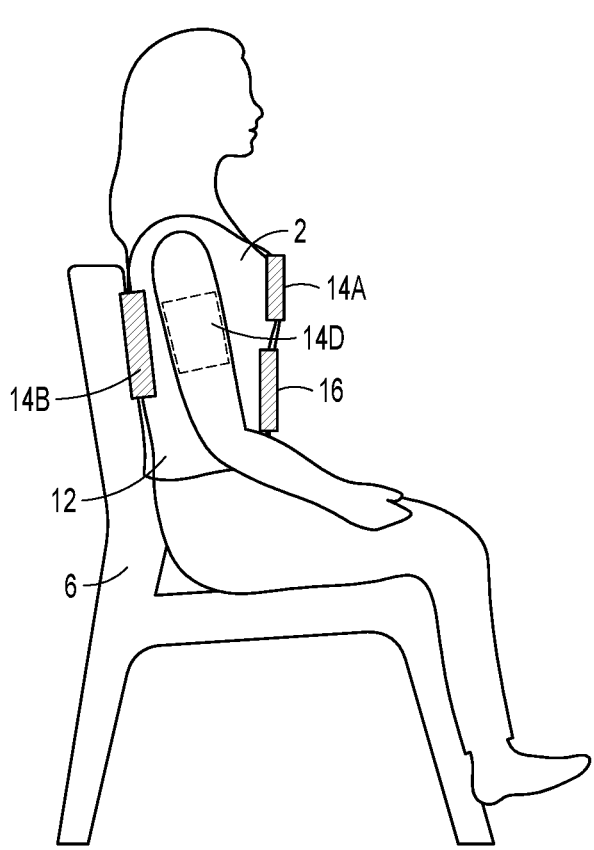
Figure 1C:
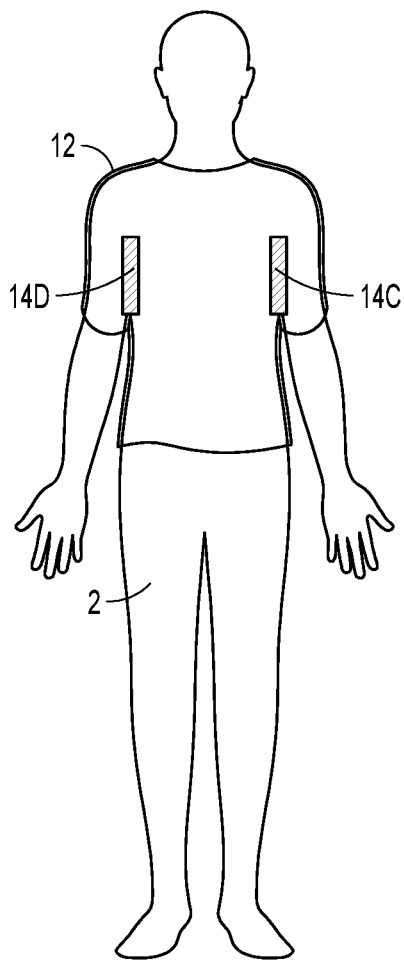

A first group or class of naturally-pressured locations are those where there is a force exerted by the body 2 on an external surface, for example, between the torso of the body 2 and a bed 4 (as in FIG. 1A) or between the torso of the body 2 and a chair 6 (FIG. 1B). A second group or class of locations are those where one part of the body 2 puts pressure on another part of the body 2. For example, when the body's arm 2 rests on its side, the body 2 puts pressure on the textile between the arm and the torso, e.g., at or below the armpit (FIG. 1C). A third group or class of locations are those where very light pressure is exerted onto the body 2, such as from the weight of a blanket 8 or even pressure due to the weight of a textile (e.g., the material of a shirt being worn by the body 2) onto the torso when the body 2 is lying down (FIG. 1A).

Often, many such pressured locations are present concurrently. For example, when sitting as in FIG. 1B, there is pressure between the body 2 and a surface of the chair 6, such as a front surface of the chair back, between the arm and torso of the body 2, and between the chest of the body 2 and a textile (such as a blanket 8 or garment). When lying down, the same set of pressured locations exist, but there is typically additional pressure between the body 2 and the bed 4 (FIG. 1A) compared to that between the body 2 and the chair back (FIG. 1B), and there can be additional pressure due to a blanket 8 or the garment itself pressing against the body 2. The inventors have even found pressure between the arm and torso and between the chest and clothing when standing and even when there is no contact with an external surface.

In conjunction, these different pressured locations present a myriad of sensing opportunities that can be leveraged to measure vital signals, such as cardiac or respiratory properties. Some devices or systems on the market have tried to accomplish this with discrete electronic components like ECG electrodes or pressure sensors. However, these discrete electronics typically loose the comfort and feel of the textile compared to the textile without the electronics present. Moreover, any time there is a noticeable change in feel (such as between a location of the textile without a discrete electronic device to a nearby location where the discrete electronic device is present), it can be particularly noticeable and a source of great discomfort for a person trying to sleep. Some other ECG devices on the market use textile-based ECG electrodes, which improve on the comfort of the electrode locations themselves but known textile-based ECG electrodes still require tightly worn clothing that is in direct contact with the skin to obtain a usable signal, which can reduce overall comfort when being worn for sleep. The requirement for a tightly-worn garment for these devices raises can also raise substantial robustness issues due to motion artifacts with dry electrodes.

The inventors have found that methods and systems that sense ballistic movements, e.g., pressure changes in the textile due to breathing and heartbeat, can overcome the limitations of existing technology described above and can measure these pressure changes to extract physiological variables. The resulting garment systems and methods described herein are a novel solution that leverages numerous contact opportunities to measure ballistic movements while being able to be incorporated in comfortable, loose-fitting textile-based sensing solutions.

There are several challenges to designing such a solution. First, there is no existing fabric-based method to sense continuous and dynamic changes in pressure. Existing textile pressure sensors are binary detectors, e.g., they detect high pressure versus low pressure, but they do not measure the amount of pressure in a continuous manner. Second, the dynamic pressure at one potential sensing location can be orders of magnitude different from another otherwise comparable sensing location. At one end of this spectrum, a substantial amount of body weight is placed on a worn textile while sleeping. At the other end, there is a minuscule amount of pressure exerted by the torso onto the textile during inhalation. Third, no single location on the body 2 has been found to provide a sufficiently good signal for robustly and accurately estimating all physiological parameters that may be of interest, and the inventors have found that in some examples, it is helpful or even necessary to measure the signal at multiple locations and fuse the information together because.

The systems and methods described herein address these challenges using several unique approaches. For locations where there is moderate to large amounts of pressure, a novel textile-based pressure sensor can be used to leverage resistive and capacitive changes to measure pressure changes, such as those that result from respiration and heart beats. For locations where there is a tiny amount of pressure but where the textile is dynamic, a triboelectric textile-based sensor can be used to leverage small amounts of compression to extract the dynamics of the textile. These sensors can be combined in a loose-fitting textile-based garment and their signals can be fused using a combination of signal processing and machine learning to enable holistic textile-based sensing of physiological variables without sacrificing comfort. The system described herein combines the novel textile-based pressure sensor and the textile-based triboelectric sensor, and fuses signals from a distributed set of sensors to extract ballistic signals from multiple locations.

The present disclosure describes a novel distributed multimodal textile-based sensor system that can be integrated with loosely-worn clothing, such as pajamas, to measure physiological signals. The system described herein can rely exclusively on textile-based elements in sensed regions, while using discrete electronic components only in locations where more rigidity is expected, such as buttons. The system comprising this combination of sensors was found to reliably detect physiological signals across diverse postures and leverage multiple forms of opportunistic contact between the textile-based garment and the wearer's body.

The present disclosure also describes a method for processing the signals from the sensors, referred to hereinafter as "the signal processing pipeline," to fuse information from multiple vantage points while considering signal quality from each sensor. This allows the extraction of precise information about physiological variables such as heart rate, inter-beat intervals, heart-rate variability, respiration rate, and body posture.

As used herein, the terms "body posture" or simply "posture" refers to the position of a particular part of the body relative to another structure or surface, which can include relative orientation of the body part of interest relative to the other structure or surface. In an example, the garment systems and methods described herein can be configured to determine a posture of a person's torso, i.e., relative to the top surface of a bed or the surface of a chair back, which might be referred to as the "posture of the torso" or the "torso posture." In another example, the garment systems and methods can be configured to determine a posture of a person's head or neck, i.e., relative to the surface of a pillow or a head rest, which might be referred to as the "posture of the head" or the "head posture." In another example, the garment systems and methods can be configured to determine the posture of one or both of a person's legs, i.e., relative to a bed or to the seat or other surface of a chair, which might be referred to as the "posture of the leg" or "leg posture." In another example, the garment systems and methods can be configured to determine the posture of one or both of a person's arms, i.e., relative to a bed or to a surface of a chair, which might be referred to as the "posture of the arm" or "arm posture."

In some examples, the garment systems described herein provide for comfortable and unobtrusive monitoring of physiological information from a wearer that can be worn continuously during long duration of wear without impacting sleep. To achieve these aims with loosely fitting textiles, the sensing substrates described herein can simultaneously capture posture information in addition to signals that contain respiration and heart rate information. Existing sensing systems fall short of these aims.

A variety of prior work has looked at using flexible but non-textile based sensors that are embedded in textiles. For example, one solution to measure vital signs uses electromechanical film (EMFi) to measure ballistic heart rate. Another solution also senses ballistics using pressure sensors printed on a polymer substrate. Several such approaches have also been presented for posture detection using smart textiles, such as: weaving a copper wire in the back of a shirt to measure varying impedance due to bending of the spine; using a plastic optical fiber to monitor spinal posture; using an array of piezoelectric sensors to determine posture. While the sensors are flexible, they are still made of stiff non-textile components that lack the feel of an everyday textile. In addition, several of these require tight contact between sensors and skin for a reliable signal, which in turn, requires tight clothing.

Other attempts have integrated discrete sensors like inertial measurement unit ("IMU") sensors and pressure switches in textile elements, primarily to obtain postural parameters. In these examples, three or more IMU sensors are used to capture spinal angle, and are placed on thoracic, thoraco-lumber, and lumber parts. However, because any movement would essentially be sensed by the IMU sensors, the garments often must be tight-fitting to avoid unwanted motion of the IMU sensors that is not associated with actual movement by the wearer. In contrast, the systems and methods described herein use no discrete sensing elements and instead directly measure ballistic signals.

Some prior work has developed fabric-based sensors for physiological sensing. However, much of the prior work on physiological sensing with fabric-based sensors has been based on tight-fitting garments typically by relying on conductive fabric electrodes. While these electrodes are widely available, they are designed for tight contact with the skin and unsuitable for loosely worn clothing. There has been some work on measuring impedance changes for physiological measurements, e.g., by integrating piezoelectric elements in a smart textile to track changes in impedance using a sinusoid injected across two fabric layers. This work also relies on tightly-worn clothing and close skin contact.

There has been limited work on sensing physiological variables using loose-fitting textiles. One such work is respiration sensing using conductive foam pressure sensors. This is essentially a binary foam-based sensor that moves between an open and short circuit configuration while a person breathes. In contrast, the systems described herein provide for complete cardiorespiratory rhythm signal while using far more natural fabric elements.

There are many wearable devices in the market for sleep sensing, most of which use photoplethysmography to measure the pulse wave on the wrist or fingers. While these devices provide good quality heart rate and breathing rate, heart rate variability is inaccurate and sleep posture is unavailable. Accurate heart rate variability (HRV) is difficult to obtain from wrist-worn wearables that measure pulse since the pulse wave has a curved peak whereas modalities like electrocardiography (hereinafter "ECG") and ballistocardiography (hereinafter "BCG") have a very sharp and pronounced peak. In addition to accuracy issues, a key distinction between these wearable devices and the systems described herein is the systems described herein can be fully integrated within existing daily wear and does not need additional wearables.

There have also been a variety of non-contact methods that have recently been tried for measuring respiration and heart rate signals. One body of work is on radar-based sensing of respiration and heart rhythm. These methods use frequency-modulated continuous wave ("FMCW") or ultra-wideband ("UWB") radar and measures changes in displacement and the doppler shifts due to respiration and ballistics of the heart. While non-contact sensing is appealing, presently robustness is a major issue due to occlusion between the sensors and the subject (e.g. from a blanket, bed structure, or clothing worn by the subject), variations in sleep posture, movement artifacts, and disaggregation of signals when multiple individuals share the same bed, just to name a few. As a result, these methods typically are more accurate for respiration sensing which causes larger movements than ballistics of the heart. Other non-contact approaches include the use of vision-based and depth camera-based methods such as use of cameras to find physiological variables. These require line-of-sight, proper lighting and a relatively stationary user within an area in front of a camera.

Several prior approaches have explored the use of instrumenting furniture including chairs and beds. Approaches in this body of work typically use discrete strain gauges and custom textiles to sense changes in pressure, such as with a textile or electronic device instrumented in a chair's seat cushion to differentiate between multiple sitting postures or extracting a pressure heat map between two sheets. Several efforts have also looked at unobtrusively instrumenting beds to measure ballistic heart rate during sleep. One approach leverages highly sensitive geophones to measure the seismic motions induced by individual heart beats and slow-moving signals from respiration. Commercial micro-electro-mechanical systems ("MEMS") accelerometer-based devices are available that can measure heart rate based on ballistocardiography signals measured via the bed.

Figure 2B:
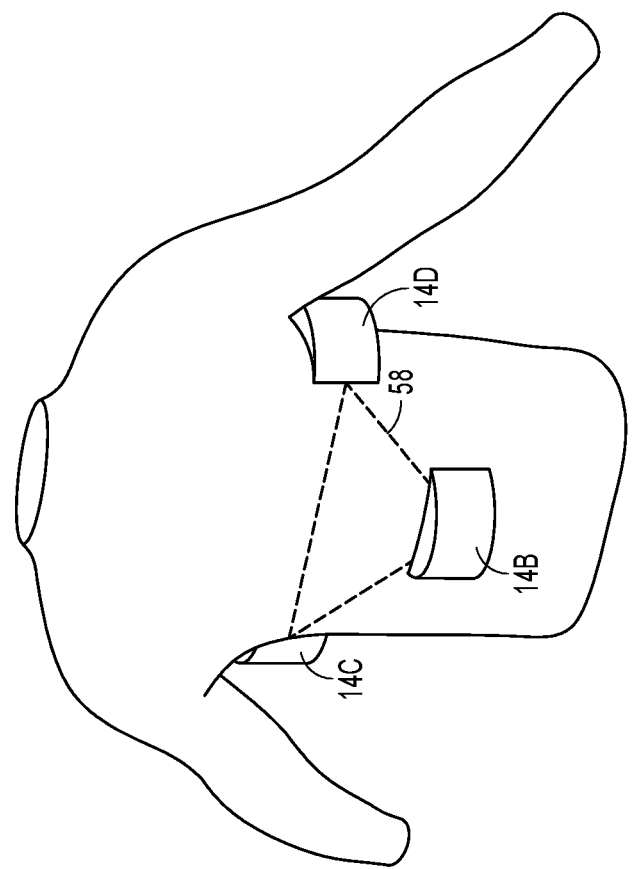
FIG. 2B is a rear perspective view of the example garment and sensors of FIG. 2A.
Figure 2A:
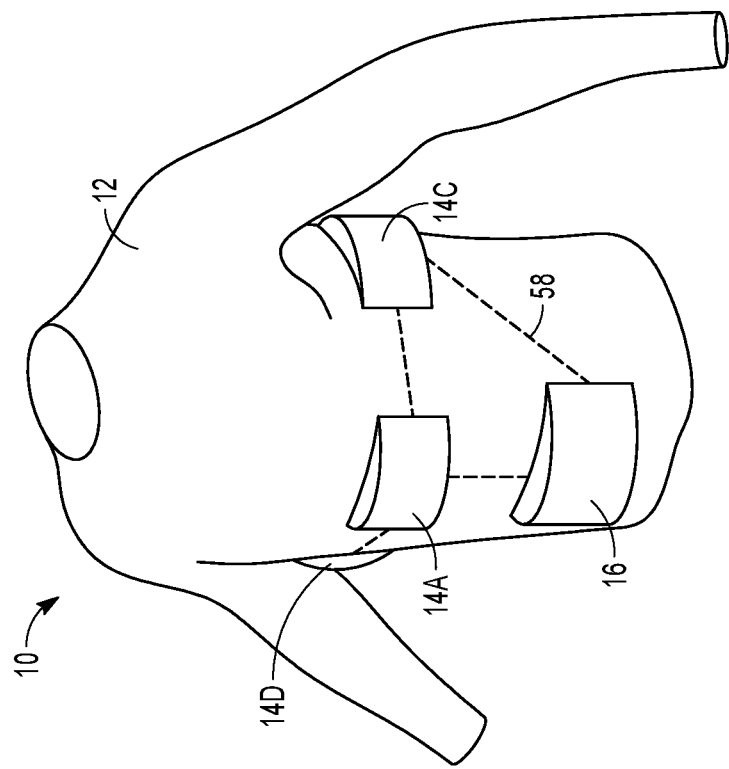
FIG. 2A is a front perspective view of an example garment with sensors for measuring physiological conditions of a wearer.

FIGS. 2A and 2B (collectively referred to as FIG. 2) shows an example textile-based system for sensing physiological conditions of a user, such as one or more of heart rate, heart rate variation, breathing rate, and posture. Some aspects of the system 10 are also shown in FIGS. 1A-1C. In an example, the system 10 includes a distributed textile-based sensor architecture that can measure cardiac and respiratory signals. The building block of the is a resistive pressure sensor that measures pressure changes. The system 10 can also include a triboelectric sensor that measures surface charge transfer to measure tiny ballistic signals, such as small ballistic changes from the heart. In an example, the system includes a garment substrate 12, also referred to herein simply as "the garment 12," which can be worn by a person of interest for which one or more physiological sensors is to be measured, also referred to herein as the "wearer."

In the example shown in FIGS. 1A-1C, 2A, and 2B the garment substrate 12 is in the form of a shirt that is worn on the wearer's torso, such as a T-shirt, for example a pajama shirt. As described in more detail below, the shirt form of the garment 12 allows the system 10 to determine, among other things, the posture of the wearer's torso relative to a supporting surface, such as However, the garment substrate 12 is not limited to a shirt, but rather could be any other conceivable type of garment that might be worn by the wearer and can be used to form a system that measures the posture of parts of the wearer's body other than the torso. For example, the garment substrate 12 could be a pair of shorts or pants that are placed over the wearer's legs and that can be configured so that the system 10 can determine a posture of one or both of the wearer's legs or hips. In another example, the garment substrate 12 could be placed on or around the wearer's head or neck, such as an eye mask or a hat for the head or a ruff or turtleneck for the neck, so that the system 10 can determine a posture of the wearer's head or neck.

In yet another example, the system 10 can include more than one garment substrate 12 to determine a posture of more than one part of the wearer's body, such as a first garment substrate 12 that is a shirt and a second garment substrate 12 that is a pair of pants (e.g., a pajama set including a pajama shirt and pajama pants). The resulting system 10 can then be configured to determine a posture of the wearer's torso and the wearer's legs and/or hips, which can provide a more complete representation of the wearer's total body position than a system 10 with only a single garment substrate 12.

One or more resistive pressure sensors 14A, 14B, 14C, 14D (referred to collectively or individually as "resistive pressure sensors 14" or simply "resistive sensor 14") are coupled to the garment substrate 12 at one or more first specified locations. In an example, a plurality of the resistive pressure sensors 14 form a distributed array of resistive pressure sensors that, collectively, can be configured to determine one or more physiological parameters of the wearer with more accuracy than might be expected from a single resistive pressure sensor 14 or a cluster of resistive pressure sensors 14 positioned in close proximity.

In an example, the system can also include one or more triboelectric sensors 16 coupled to the garment 12 at one or more second specified locations. The system 10 can also include electronics (not shown in FIGS. 2A and 2B) configured to process signals from the one or more resistive pressure sensors 14, and if present the one or more triboelectric sensors 16, to determine one or more physiological properties of a wearer of the garment 12. In an example, the electronics are configured to process signals from a distributed array of a plurality of the resistive pressure sensors 14 to determine, among other things, a posture of the portion of the wearer's body on which the garment 12 is positioned.

As used herein, the term "textile" or "textile-based," when referring to the substrate that forms each of the one or more layers of the resistive sensor 14 or the triboelectric sensor 16 and/or to the resulting functionalized textile garment 12, refers to a structure comprising one or more fibrous structures, and in particular to threading or thread-like structures (such as yarns, threads, and the like), arranged to collectively form a bendable, sheet-like layer of cloth or cloth-like material (such as by weaving or otherwise combining the one or more fibrous structures into a cloth layer). "Textiles" commonly refers to materials that form the cloth layers of a garment or other apparel, although the present description is not limited merely to "textiles" that are typically used for garment or apparel fabrication. That being said, in some examples, the substrates that are used to form each of the sensors may be a conventional, off-the-shelf woven or non-woven fabric, such as cotton or bast-fiber fabric.

In an example, the system 10 includes several textile-based sensors 14, 16, also sometimes referred to herein as "patches," to enable measurement of physiological signals from multiple vantage points. For example, as shown in FIG. 2, the system can include a garment 12, such as a shirt 12, for example a pajama shirt 12, with two or more textile-based sensors attached thereto. In the example shown in FIG. 2, the system 10 includes resistive sensors 14 configured to measure the local pressure being applied onto the resistive sensor and one or more triboelectric sensors 16 to measure small ballistic signals from the wearers heart. The system 10 shown in FIG. 2 includes a first resistive sensor 14A located on a front panel of the garment 12 proximate to the wearer's chest, a second resistive sensor 14B located on a rear panel of the garment 12 proximate to the wearer's lower back, a third resistive sensor 14C located on the left side of the garment 12 underneath the left sleeve proximate to the wearer's left armpit, and a forth resistive sensor 14D located on the right side of the garment 12 underneath the right sleeve proximate to the wearer's right armpit, also referred to as the front resistive sensor 14A, the rear resistive sensor 14B, the left resistive sensor 14C, and the right resistive sensor 14D, respectively. The system 10 also includes a triboelectric sensor 16 located on the front panel of the garment 12 proximate to the wearer's belly.

Resistive Sensor

Figure 3:
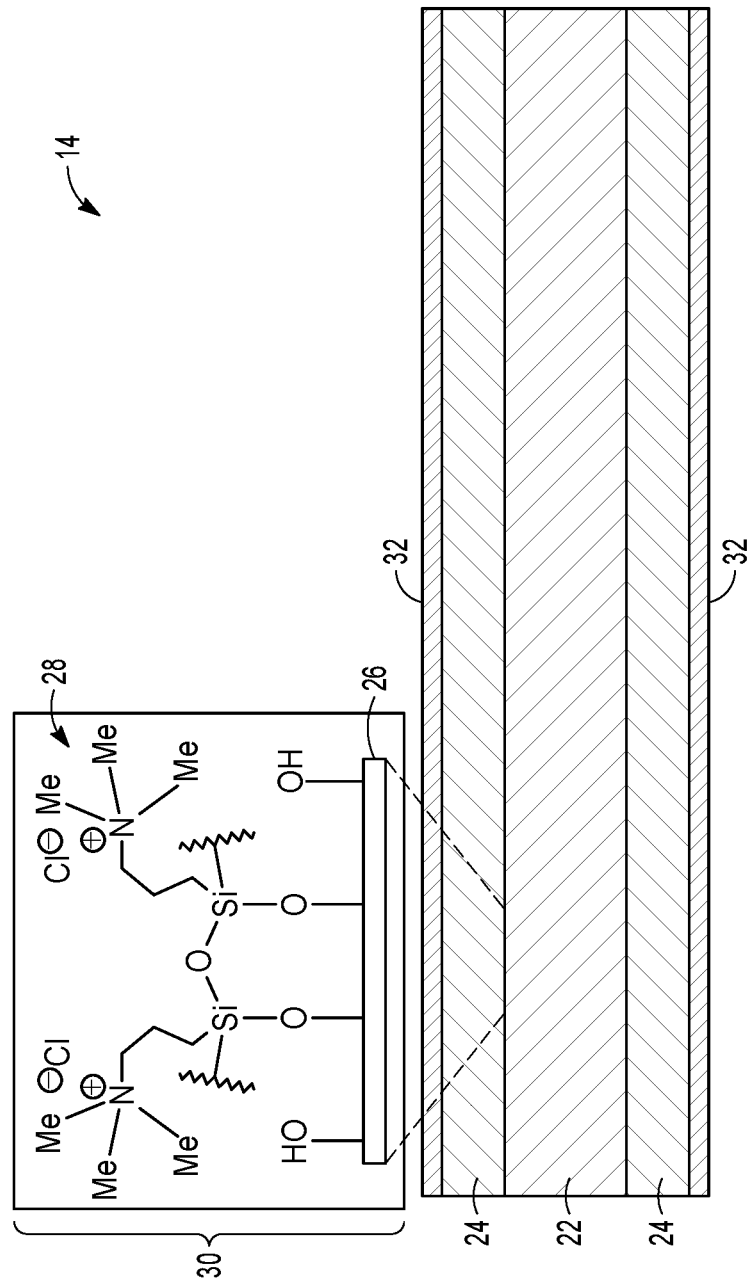
FIG. 3 is a cross-sectional view of an example resistive sensor configured to measure static pressure changes for the example textile-based systems of FIGS. 1A-1C, 2A, and 2B.

FIG. 3 shows a cross-sectional view of an example resistive sensor 14 that can be used as any one of the resistive pressure sensors 14A, 14B, 14C, and 14D in the garment system 10 of FIGS. 2A and 2B. In an example, the resistive sensor 14 includes one or more highly-resistive inner layers 22 sandwiched between two conductive outer layers 24. As used herein, the term "highly-resistive" refers to a structure with an overall resistance of 1 Mega-ohms (MΩ) or more. As used herein, the term "conductive" refers to a structure that is relatively free to conduct electrical current therethrough, for example a structure with a resistance of 100Ω or less.

In an example, the highly-resistive inner layer 22 is formed from one or more textile-based layers. However, the design of the inner textile-based layer 22 is not straightforward as it would seem because the ballistic signal due to a wearer's heart rate is extremely weak. If the textile substrate is an insulator like regular cotton, then the resistance is extremely high (e.g., on the order of teraohms) and it is extremely complex and expensive to design a sensing circuit to measure minute resistance changes at such high electrical impedance. High impedance can be desirable in the circuit to measure changes in a high impedance sensor, but this makes the circuit very sensitive to noise, e.g., a small current induced on a high-impedance circuit results in higher noise voltage than the same noise on a low impedance circuit. There can be many sources of noise in fabric-based circuits that use large conductive layers, such as electromagnetic noise, static fields, and motion artifacts. Therefore, the inventors have found it can be advantageous to operate in a lower impedance regime to minimize the impact of noise on the signal. On the other hand, if the textile-based inner layer 22 is too conductive, then it can short too easily after a small amount of pressure is applied and may not be able to cover the range of pressures that are typical in clothing, particularly clothing that is worn during sleep. The pressure between the body 2 and an external surface can vary by more than an order of magnitude depending on whether an individual is seated or lying down. Similarly, the pressure between a wearer's arm and torso is also much smaller than the pressure between the body 2 and a bed or a chair. Thus, the inventors have found that the textile-based inner layer 22 should operate in a "sweet spot" where the fabric is optimized with sufficiently high resistance so that it does not create a short circuit even under pressure while at the same time having a resistance that is low enough so that it will be sensitive to small pressure changes due to the ballistics of the heart.

From a fabric functionalization perspective, it is also desirable to provide for enhanced wash stability of the fabric, e.g. so that the resistive sensor 14 will be resistant to repeated wash cycles as well as demands due to sweating, rubbing, and aging of fabric. But methods to functionalize the fabric to increase wash stability tend to also impact the resistivity of the fabric, resulting in two challenges: (1) ensuring wash stability so that the impedance of the resistive sensor 14 is stable across wash cycles, and (2) finding coatings that keep the overall resistivity of the resistive sensor 14 within desired limits.

In an example, the inner layer 22 comprises one or more functionalized textile layers comprising a textile substrate 26 (shown in the inset of FIG. 3), such as a cotton fabric, onto which has been applied one or more functionalized coating materials 28 to form one more functionalized coating layers 30. The functionalized coating material 28 allows the resistivity of the resulting functionalized inner layer 22 to be proportional to the pressure being applied to the resistive sensor 14. In an example, the one or more functionalized coating materials 28 modify surface resistivity of the inner layer 22 compared to the textile substrate 26 without the functionalized coating 30. In some examples, a functionalized coating 30 is not necessary, e.g., if the textile-based substrate 26 itself has a resistivity value that is within a desired range.

In some examples, the one or more functionalized coating layers 30 are applied via vapor deposition onto the textile substrate 26. In an example, the functionalized coating material 28 comprises a hydrophobic, perfluorinated alkyl acrylate that can be vapor deposited onto the textile substrate 26 with a vacuum reactor deposition chamber to provide a perfluorinated coating 30. The perfluorinated alkyl acrylate coating material 28 imparts wash stability to the inner layer 22. A perfluorinated coating 30 are superhydrophobic and are commonly used to create stain-repellant and sweat-repellant upholstery and active wear. In some examples, however, a perfluorinated alkyl acrylate surface coating 30 resulted in the inner layer 22 having increased resistivity as compared to a pristine, e.g., non-coated, textile substrate 26. Therefore, in another example, the chemical structure of the point where the coating 30 is chemical grafted onto the textile substrate 26 includes a siloxane moiety, which was found to not attenuate the high surface resistivity observed with perfluoroalkyl coatings. Without wishing to be bound by any particular theory, the inventors hypothesize that such increases in surface resistivity evolved because perfluoroalkyl coatings contained saturated alkyl chains without accessible conductive states. As most textile coatings are similarly insulating, the inventors believed that a surface coating that imparts either electronic or ionic conductivity to the textile substrate of the inner layer 22, such as the coating material 28 comprising the siloxane moiety, is beneficial.

In yet another example, the functionalized coating material 28 comprises an ion-conductive coating material 28 because ionic conductors are comparatively more compatible with salt-rich biological systems than electronic materials. One example of an ion conductive coating material 28 that can be used is a siloxane containing quaternary ammonium moieties, such as N-trimethoxysilylpropyl-N,N,N,-trimethylammonium chloride, as shown in the inset of FIG. 3. The siloxane moieties were found to covalently bond to free hydroxyl groups present in the repeat unit of cellulose acetate (e.g., cotton) on the surface of the textile substrate 26, while the quaternary ammonium moieties and their chloride counterions act as ion conductors that reduce the observed surface resistivity of the textile substrate 26. The surface resistivity of the coated inner layer 22 is proportional to the surface concentration of the quaternary ammonium groups, which, in turn, is proportional to the concentration of the siloxane molecule used during the solution-phase functionalization reaction that forms the functionalized coating 30.

Another example of an ion-conductive material that can be used as the coating material 28 comprises a highly p-doped poly(3,4-ethylenedioxythiophene) (also referred to herein as "p-doped PEDOT" or simply "PEDOT"). In an example, the p-doped PEDOT is uniformly or substantially uniformly charge balanced with one or more counterions. In an example, the counterions comprise chloride counterions. In an example, the concentration of chloride ions is about $10^{10}$ ions per cubic centimeter (cm$^3$) and a concentration variation of ± about 103 ions per cm$^3$. In another example, the counterion comprises at least one of bromide, iodide, sulfate, acetate, formate, lactate, or combinations thereof.

In an example, the PEDOT polymer that is used for the coating material has the structure of formula [A]:

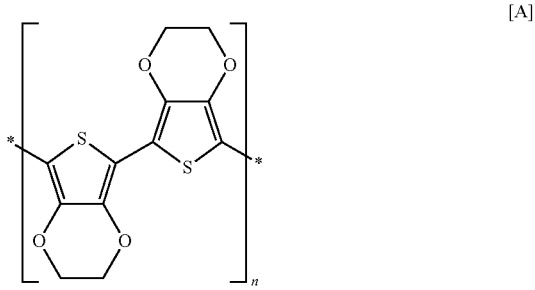

[A]

where "n" is the number of repeat units. In an example, n can be 20 or more, for example 30 or more, such as 40 or more. In an example, n is from about 20 to about 10,000, for example from about 50 to about 9,000, such as from about 100 to about 8,500.

Further details of one example method of applying PEDOT to a textile substrate is described in U.S. Patent Application Publication No. 2019/0230745 A1, titled "ELECTRICALLY-HEATED FIBER, FABRIC, OR TEXTILE FOR HEATED APPAREL," published on Jul. 25, 2019 and filed on Jan. 25, 2019, the disclosure of which is incorporated herein in its entirety by reference.

In examples where the coating material 28 comprises the p-doped PEDOT, the resulting coating 30 can have an electrical resistance of from about 0.1 to about 10,000 Ohms per square inch (Ω/in$^2$). In an example, the coating 30 formed from the PEDOT has a thickness of from about 100 nanometers (nm) to about 10,000 micrometers (μm) or about 10 millimeters (mm), such as from about 100 nm to about 1 μm. In an example, the coating 30 formed from the PEDOT coating material 29 are uniformly or substantially uniformly p-doped throughout the entire volume of the coating 30, as revealed by bulk optical absorption measurements.

The weave density of the textile substrate 26 can also affect the overall resistivity of the resistive pressure sensor 14. In an example, the textile-substrate 26 comprises a cotton gauze substrate with a medium weave density. The inventors found that a medium weave density minimized the occurrence of shorting events in the inner layer 22 and provided for the most stable pressure-induced electrical signals while remaining comfortable to wear after being functionalized and incorporated into the garment 12.

In an example, each of the conductive outer layers 24 are formed from one or more textile-based layers so that the resistive sensor 14 will be an "all-textile" sensor. In an example, each of the conductive outer layers 24 comprises a silver nylon. The conductive outer layers 24 act as the electrodes of the resistive sensor 14, which can be connected to a detection and amplification circuit (described in more detail below).

In an example, various test sensors of the same size were created by sandwiching a sheet 22 of cotton (either pristine or functionalized with an ion-conductive coating 28) between two silver nylon fabric layers 24. As discussed above, examples where the cotton gauze substrate 22 is functionalized with N-trimethoxysilylpropyl-N,N,N,-trimethylammonium chloride displayed a more sensitive voltage change with applied pressure as compared to a pristine cotton gauze or cotton lycra substrate 26. Therefore, three-layer devices containing an ion-conductive cotton gauze proved to be efficient and simple sensor of applied pressure.

In an example, the functionalized coating 30 was shielded with an optional protective coating 32, to impart wash stability to the resistive sensor 14. In an example, the protective coating 32 comprises a hydrophobic material, such as a perfluorinated siloxane coating, which can be deposited through vapor deposition to form the protective layer 32. The protective coating 32 offers an effective barrier against any degradation of properties in the fabric resistive sensor 14 caused by the wearer sweating, washing, rubbing and any other aging processes.

The ion-conductive coating 30 of the functionalized inner layer 22 is different from previously-known commercial textile coatings, which have typically been applied to impart hydrophobicity (e.g., for stain-repellent fabrics) or to create antimicrobial material. For both hydrophobic and antimicrobial functionality, known coating materials are electrically insulating and, therefore, previously-known iterations of functionalized textiles are not usable in the design of the resistive sensor 14.

In an example, the resistive sensor 14 comprises one or two layers of ion-conductive functionalized cotton gauze as an inner layer 22, sandwiched between two sheets 24 of silver-plated nylon fabric. All the textiles were sonicated in water for 15 min, and then rinsed with isopropanol and dried in the air prior to use. To chemically graft the surface of the cotton gauze substrate 26, the cotton gauze substrate 26 was soaked in N-trimethoxysilylpropyl-N,N,N,-trimethylammonium chloride dissolved in isopropanol (15:100 V/V), which is a precursor to the functionalized coating material 28 on the inner layers 22, for 30 min and then cured at 100° C. for 2 hours to form the functionalized coating 30, followed by rinsing with isopropanol and drying in air. The surface of the functionalized cotton gauze was then modified with a vapor deposition of trichloro(1H,1H,2H,2H-perfluorooctyl) silane to form a hydrophobic protective coating 32, which provides the sensor 14 with washability and durability. In an example, the 30-min deposition of the coating material 28 was conducted in a custom-built, round shaped reactor (290 mm diameter, 70 mm height) under vacuum conditions, e.g., at the constant pressure of about 1 Torr absolute. The functionalized cotton gauze 22 was then cut into eight 10 cm by 6 cm sheets, each of which was sewn around the perimeter between two corresponding 8 cm×4 cm sheets 24 of silver fabric. Sewing together each pair of these joined gauze-silver sheets yielded four resistive sensors 14 each having the three-layer structure shown in FIG. 3.

Figure 4:
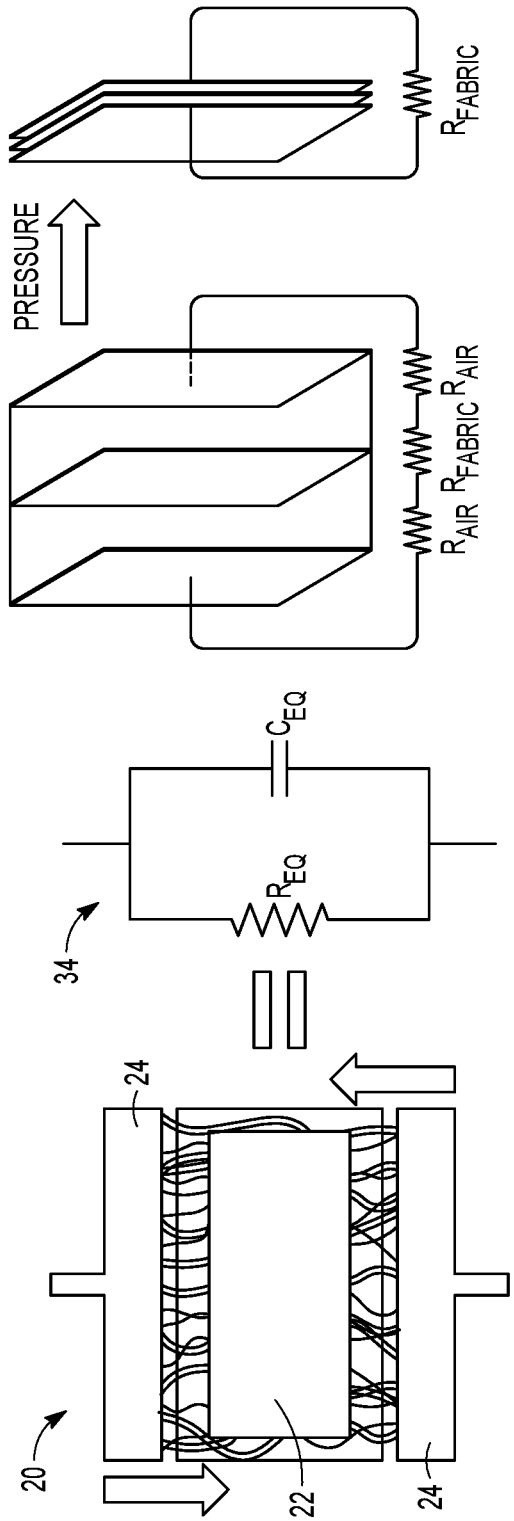
FIG. 4 is a schematic diagram of an equivalent circuit model for the example resistive sensor of FIG. 3.

An electrical model of the resistive sensor can be useful in explaining and understanding its behavior under pressure. FIG. 4 shows the structure of the three-layered resistive sensor 14 and its electrical equivalent model 34. The resistance of the functionalized inner layer 22 is high enough so that it can measure a wide range of pressures but low enough so that moderate-sized resistors can be used in the circuit to minimize noise.

The resistance through a transmission medium is inversely proportional to the thickness of the medium, as seen in Equation [1].

$$R_{eq} = \rho \frac{1}{A} \quad [1]$$

where $\rho$ is electrical resistivity, l is the length, and A is the cross-sectional area of the medium. In the resistive sensor 14, l is equal to the thickness of the functionalized inner layer 22, e.g., $R_{fabric}$ in FIG. 4.

In order to determine what aspects of applied pressure can be measured, it is helpful to see how the resistive sensor 14 works under pressure. Upon application of an inward pressure on the two outer layers 24, two simultaneous or substantially simultaneous phenomena occur. First, the number of resistive routes between the two conductive layers 24 increases because the air gap between the outer layers 24 is reduced. At the same time, the thickness of the inner layer 22 is reduced, and the capacitance $C_{EQ}$ of the resistive sensor 14 changes. Both of these factors contribute to reduction in impedance of the sensor 14 as a result of the increase in pressure.

From a measurement perspective, it is much simpler to design a circuit to measure resistance changes than capacitance changes, therefore, in an example, resistance changes were used to measure a ballistic signal. To follow the pressure applied on the sensor 14, a voltage divider was used to produce a voltage that follows the changes in resistance of the sensor 14. This voltage contains information about the pressure applied to the portion of the garment 12 where the sensor 14 is positioned. However, it is too coarse grained to be useful for extracting vital signs. In an example, the signal is filtered and amplified in the analog domain before being used for respiration and heartbeat detection (as described in more detail below).

Figure 5:
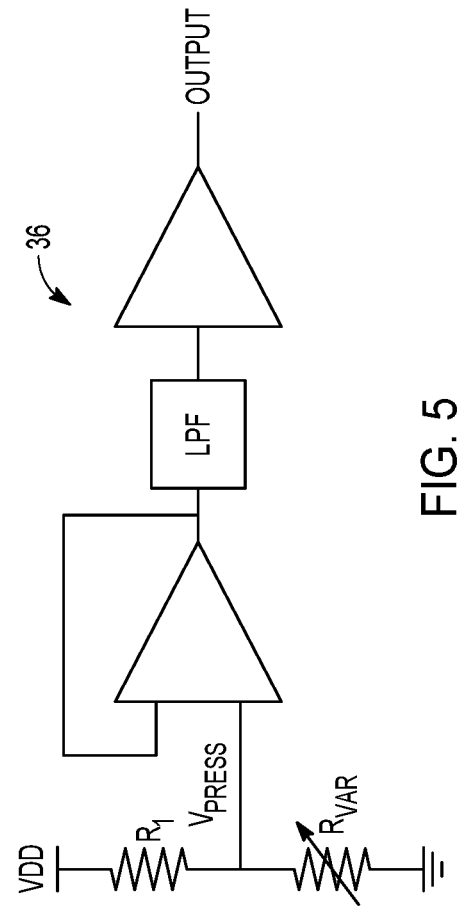
FIG. 5 is a schematic diagram of an amplification circuit configured to provide a measurable signal from the example resistive sensor of FIG. 3.

FIG. 5 shows a schematic diagram of a circuit 36 for the resistive sensor 14 of FIG. 3. Due to the very small signal generated by heartbeats, it was desirable to increase sensitivity from the source. In other words, the design was tuned in such a way that changes in the resistance of the resistive sensor 14 ($R_{var}$) can cause maximum possible impact on the output voltage ($V_{Press}$). As such it is desirable to increase $\partial V_{press}/\partial R_{var}$ as found by Equation [2].

$$V_{Press} = V_{dd} \times \frac{R_{var}}{R_{var} + R_1} \quad [2]$$

$$\rightarrow \frac{\partial V_{Press}}{\partial R_{var}} = V_{dd} \times \frac{R_{var}}{(R_{var} + R_1)^2}$$

Equations [1] and [2] show that sensitivity decreases as $R_{var}$ increases. Maximum sensitivity is achieved when $R_{var}$ is much smaller than $R_1$ in the circuit 36. Of course, this can be achieved by choosing an extremely large $R_1$. Very large output resistance of the sensor 14, however, can result in a substantial amount of noise being injected into the electronics circuit 36. Therefore, the inventors believe that a more sensible approach is to decrease the resistance of the functionalized inner layer 22 so that the resistance of the inner layer 22 is carefully tuned into the desired regime.

To be most effective, each resistive sensor 14 is placed at a location where the garment 12, and hence the resistive sensor 14, will experience some appreciable amount of baseline pressure by being compressed between two larger structures, such as between the wearer's body 2 and another surface. For example, as shown in FIGS. 1A-1C, 2A, and 2B, the garment system 10 can include the front resistive sensor 14A coupled to a front fabric layer of the garment 12 and the rear resistive sensor 14B coupled to a rear fabric layer of the garment 12. As shown in FIGS. 1A and 1B, the rear resistive sensor 14B can obtain a baseline pressure from the compression between the wearer's body 2 and the bed 4 when she is lying down (FIG. 1A) or with a back of the chair 6 in which she is sitting (FIG. 1B). In both scenarios, the pressure is generated by the weight of the wearer's body 2 and a normal force exerted by the supporting object (e.g., the chair or the bed). The front resistive sensor 14A can obtain a baseline pressure from the weight of the blanket 8 or other covering onto a supine wearer's body 2 (FIG. 1A) or between the wearer's body 2 and the bed 4 when the wearer is lying prone (i.e., face down, not shown).

In another example, best seen in FIGS. 2A and 2B, the system 10 can include the left resistive sensor 14C that will be pressed between the wearer's left arm and the left side of the wearer's torso and the right resistive sensor 14D that will be pressed between the wearer's right arm and the right side of the wearer's torso. Each of the left resistive sensor 14C and the right resistive sensors 14D can be located either on the textile that forms the side of the torso part of the garment 12 or on the textile that forms the inside part of the arm of the garment 12. For both the left resistive sensor 14C and the right resistive sensor 14D, the baseline pressure is obtained from the pressure between the wearer's arm and the torso caused by the weight of the arm.

Triboelectric Sensor

As noted above, the other type of sensor that is used in the garment system 10 of FIGS. 1A-1C, 2A, and 2B is a triboelectric sensor that is configured to measure ballistics under very low-pressure situations, such as when the fabric upon which the triboelectric sensor is attached is resting on a wearer's torso when the wearer is standing, sitting, or lying down. In particular, the triboelectric sensor can be configured such that it can detect small ballistics signals due to the wearer's heartbeats. Even though the magnitude of positional change due to the wearer's heartbeat is quite small and is imperceptible to the naked eye, the dynamic change is quite large due to rapid changes in flow resulting in a strong ballistic force on the chest wall of the wearer.

Figure 6:
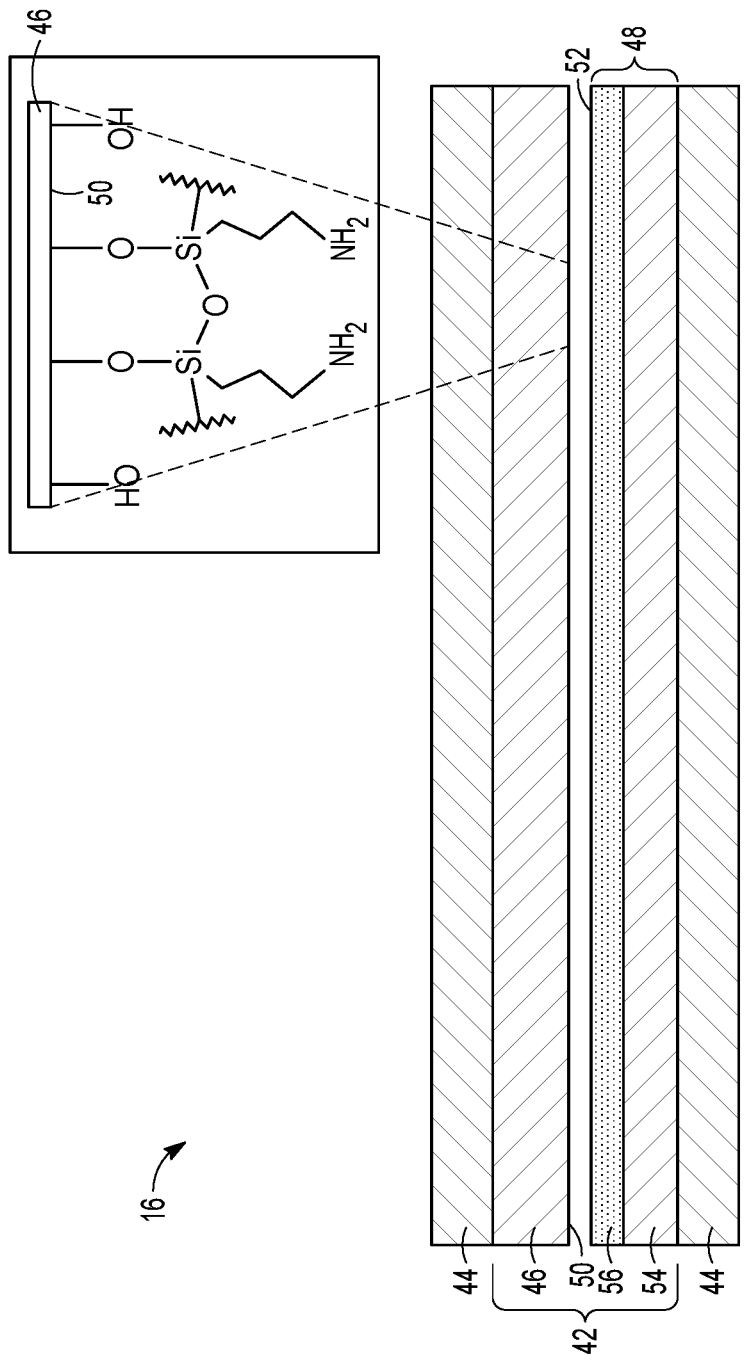
FIG. 6 is a cross-sectional view of an example triboelectric sensor configured to measure dynamic ballistic signals for the example textile-based systems of FIGS. 1A-1C, 2A, and 2B.

FIG. 6 is a cross-sectional view of an example triboelectric sensor 16 that can be used in the garment system 10 of FIGS. 1A-1C, 2A, and 2B. In an example, the triboelectric sensor 16 includes a dual-layered triboelectric core 42 (also referred to herein as "the triboelectric core 42" or simply "the core 42") sandwiched between two conductive outer layers 44. In an example, the triboelectric core 42 includes two layers 46, 48 that act as a pair of dielectric layers made from different dielectric materials (also referred to as "the dielectric layers 46, 48"), such that one of the layers transfers charge to the other layer due to the triboelectric effect when the triboelectric sensor 16 moves.

The conductive outer layers 44 act as the electrodes of the triboelectric sensor. The conductive outer layers 44 can be similar or identical to the conductive outer layers 24 of the resistive sensor 14 shown in FIG. 3, such as by being made from a silver nylon fabric. The conductive outer layers 44 can be connected to a detection and amplification circuit (described in more detail below).

Figure 7:
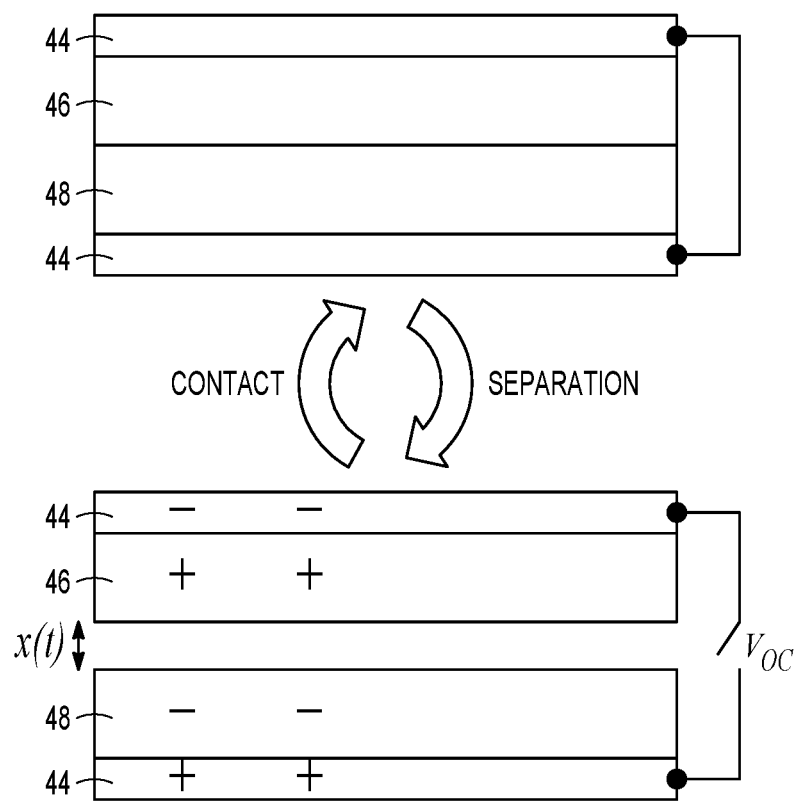
FIG. 7 is a conceptual cross-sectional view showing the operating principle of the example triboelectric sensor of FIG. 6.

When the two dielectric layers 46, 48 of the core 42 come into contact, static charging occurs over the contacting surface area. Overall, the charge on the triboelectric sensor 16 remains at zero due to the charges being located in or substantially in the same plane. Upon subsequent separation of the dielectric layers 46, 48, which results in a separation of the charges, an alternating current between the conductive outer layers 44 is induced to compensate for the charge imbalance, with the generated charges being collected on the conductive outer layers 44, as shown conceptually in FIG. 7. The open-circuit voltage $V_{OC}$ is dependent on the surface charge density ($\sigma$), the separation distance between the dielectric layers (x(t)), and the permittivity of free space ($\epsilon_0$), as shown in Equation [3].

$$V_{OC} = \frac{\sigma x(t)}{\varepsilon_0} \quad [3]$$

The operation of the triboelectric sensor 16 can be maximized when the charge transfer between the dual layers 46, 48 of the core 42 is optimized, preferably such that the charge transfer is as high as is practical. When optimizing the triboelectric sensor 16 for sensing, the parameter that can be modified is the surface charge density ($\sigma$), since this defines the overall sensitivity of the magnitude of generated voltage to joint motion (x(t)). Specifically, the voltage generated by the triboelectric sensor 16 is related to the speed of contact and separation between the two layers 46, 48 of the core 42, which allows for the detection of ballistic changes due to heartbeats.

As is known from an understanding of the triboelectric effect, the surface charge density a can depend on the materials used to form the two dielectric layers 46, 48 of the triboelectric core 42. In an example, the first layer 46 of the triboelectric core 42 comprises a positively-charged triboelectric surface 50, also referred to as "the positive triboelectric surface 50" or "the positively-charged surface 50"). Because of its charge, the first layer 46 may also be referred to herein as "the positively-charged triboelectric layer 46" or "the positive triboelectric layer 46." In this example, the second layer 48 of the triboelectric core 42 comprises a negatively-charged triboelectric surface 52, also referred to as "the negative triboelectric surface 52" or "the negatively-charged surface 52"). The negative triboelectric surface 52 is adjacent and proximate to (or in contact with) the positively triboelectric surface 50 of the positive triboelectric layer 46. Because of its charge, the second layer 48 may also be referred to herein as "the negatively-charged triboelectric layer 48" or "the negative triboelectric layer 48."

In an example, the positive triboelectric layer 46 comprises a cotton or cotton lycra based substrate, which can be further functionalized to improve charge transfer. In an example, the cotton or cotton lycra based substrate is functionalized with one or more silane moieties, such as a silane moiety comprising an amine group to act as the positively-charged triboelectric surface 50, for example an aminopropyl siloxane, as shown in the inset of FIG. 6. In an example, the negative triboelectric layer 48 comprises a fabric substrate 54 that is coated with a negative triboelectric material 56, such as polyurethane. In an example, the negative triboelectric material 56, e.g., the polyurethane, is coated onto a ripstop nylon substrate 54. The inventors found that the polyurethane coating 56 on the substrate 54, such as the polyurethane coating 56 on the ripstop nylon substrate 56, displays a negative surface charge value, on average, under the conditions in which the triboelectric sensor 16 will typically experience because of the presence of the negative triboelectric material 56, i.e., polyurethane.

When the positively-charged triboelectric surface 50 comes into contact with the negatively-charged triboelectric surface 52 and the dual layers 46, 48 of the triboelectric core 42 are sandwiched between the conductive outer layers 44, it forms a triboelectric device that can act as the triboelectric sensor 16. When pressure is applied to this triboelectric sensor 16, the two oppositely-charged layers 46, 48 are forced into physical contact, upon which a small amount of surface charge transfer occurs, creating an observable electrical signal. However, this charge transfer event is quickly reversed such that the signal quickly decays, even if constant pressure is applied to the triboelectric sensor 16. Due to this behavior, the triboelectric sensor 16 is well suited for detecting dynamic changes in pressure, such as those that can occur as a result of the ballistics of the heart.

In an example, the triboelectric sensor 16 comprises a polyurethane-coated ripstop nylon as the negative triboelectric layer 48. To provide a cotton lycra with a positively-charged triboelectric surface 50, the cotton lycra fabric was soaked in (3-aminopropyl) trimethoxysilane in a hexane solvent (10:100 V/V) for 30 min, followed by rinsing with isopropanol and drying in air, to provide a functionalized positive triboelectric layer 46. The positive triboelectric layer 46 and the negative triboelectric layer 48 were then cut into 17 cm by 13 cm sheets and sewn together as they were being placed between two 15 cm×11 cm sheets of silver nylon fabric 44.

Two Complimentary Sensor Types

As described above, both the resistive sensor 14 and the triboelectric sensor 16 can detect a cardiac ballistic signal. However, in some preferred examples, the garment system 10 includes both a resistive sensor 14 and a triboelectric sensor 16. The reason for using both sensors 14, 16 rather than just the resistive sensor 14 or just the triboelectric sensor 16 is because the resistive sensor 14 can operate under pressure, i.e. it can measure ballistics when a sufficient baseline pressure has been exerted on it. In contrast, the triboelectric sensor 16 is able to operate under very light pressure, for example, due to the weight of the textile material of the garment resting on the wearer's body 2 or the weight of a blanket 8 resting on top of the garment system 10 and the wearer. Under higher pressure, there is insufficient change in distance between the core layers 46, 48 of the triboelectric sensor 16 to cause measurable change in charge transfer. Thus, the two types of sensors are complementary and cover medium to high pressure situations (with the resistive sensor 14) and low-pressure situations (with the triboelectric sensor 16).

Assembling the Garment System

Having designed the individual textile-based sensors 14 and 16, as described above, the sensors 14, 16 were interconnected with one or more conductors 58 in a way that reduces and, in some examples, minimizes the number of discrete hard electronic components. In an example, the garment system 10 is designed for maximum comfort, particularly when the garment 12 is designed for measurement of physiological conditions while the wearer is sleeping. Therefore, in some examples, the use of metal wires as one of the conductors 58 was avoided and, in some examples, the garment system 10 is completely devoid of wires. Instead, in an example, the one or more conductors 58 of the garment system 10 are conductive threads shielded by normal cotton to act as signal conductors through the garment 12. In one example, silver-plated nylon threads 58 were used as the conductors 58. The threads 58 were shielded in a fabric rod made from cotton and attached to the conductive outer layers 24 of the resistive sensors 14 and the conductive outer layers 44 of the triboelectric sensor 16 via snap buttons.

Using these conductors 58 (e.g., the conductive thread), the sensors 14, 16 can be connected to two circuit boards depending on whether the sensor being connected is one of the resistive sensors 14 or the triboelectric sensor 16. While these can potentially be combined into a single platform, two separate circuit boards were used in an example for ease of prototyping. The circuit boards were designed with a small form factor, roughly the size of quarter or a large button. The inventors believe that the size can be further shrunk down to half the current size or smaller after further engineering and due to the capabilities of mass production version individual prototype fabrication. It is believed that in some examples, the sensors 14, 16 can be integrated into the buttons or other common hard structures of the garment 12.

In an example, the PCB board for the resistive sensors 14 is a single custom-designed PCB board that performs the filtering, amplification, and communication (described below). BCG signals are typically within the 1-10 Hz frequency range, and the peak power of the BCG signal is typically in the 7-8 Hz frequency bin. This information was leveraged to choose a cutoff frequency of 4-10 Hz for faster DC rejection and capturing the strongest BCG frequency component.

Figure 10:
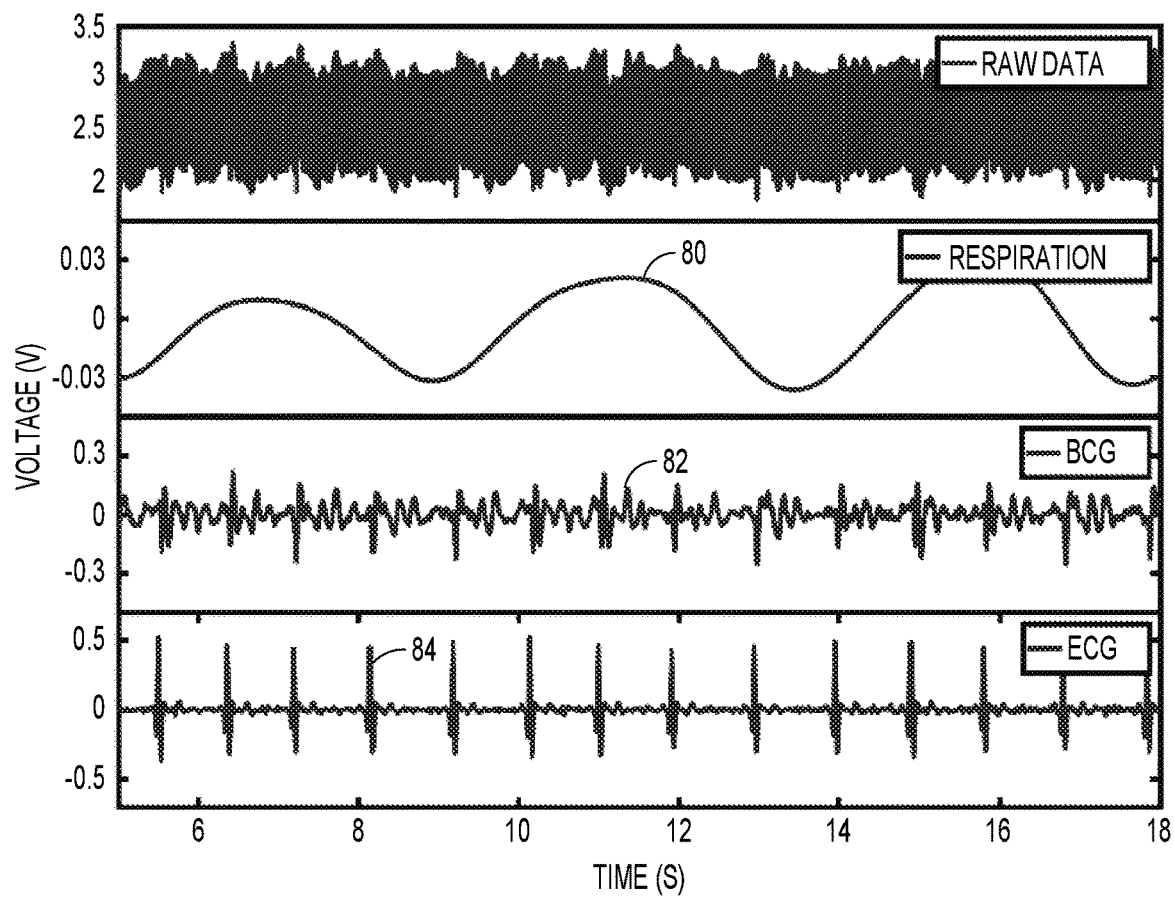
FIG. 10 is a graph comparison of the raw output signal from the resistive sensor of FIG. 3, the respiration signal and the ballistocardiograph (BCG) signal extracted from the raw signal using the example signal processing pipeline of FIG. 8, and the ground truth electrocardiograph (ECG) data during the same time period.

Another challenge for the garment system 10 is the removal or minimization of noise in indoor environments. As can be seen in FIG. 10, an example raw signal obtained from the sensors 14, 16 contains strong power line noise. The inventors believe that the substantial power line noise is due to several reasons, including the very large sensor output impedance, large sensor surface, as well as close proximity to the wearer's body 2. While typical ECG processing boards filter power line noise using a differential amplifier, the asymmetry in exposure of the conductive layers 24 (one exposed outside and the other inside) made it difficult or impossible to fully suppress noise using this method. Therefore, in an example, a 5th-order low pass filter was designed to reject power line noise. In an example, the gain of the board is around 50 dB. Each pressure sensing sensor 14 is connected to one analog pipeline drawing around 150 μA of current.

A second PCB board was designed for triboelectric signal amplification. In an example, this amplification board comprises a differential amplifier followed by multiple filtering and amplification stages to capture small movements of the ballistic signal. In an example, the cutoff frequency of the triboelectric sensor board is 4-10 Hz. Since the triboelectric sensor 16 experiences very minute movements of the skin, the gain is about 80 dB, which is larger than the resistive sensor board. The overall current consumption of the triboelectric sensor board is around 2 mA.

Optimizing Sensor Placement

The location of the sensors can be an important factor in the performance of the garment system 10 because the signal detected by each type of sensor 14, 16 is sensitive to placement. While this process may eventually be optimized to different body types or even personalized, in one example sensor placement was optimized with respect to one individual wearer (also referred to as the calibrating wearer) and used the same settings across various other wearers.

To find the best placement for the resistive sensors 14A and 14B on the front and rear of the garment 12, resistive sensors 14 were placed at different locations and the signal quality was measured while the calibrating wearer was lying down face down (prone) and face up (supine), respectively. The measurement setup was carefully done to minimize folds in the textile of the garment 12 and random body movements so that the effect of the position of the sensors 14, 16 on the BCG output signal could be isolated.

Figure 14:
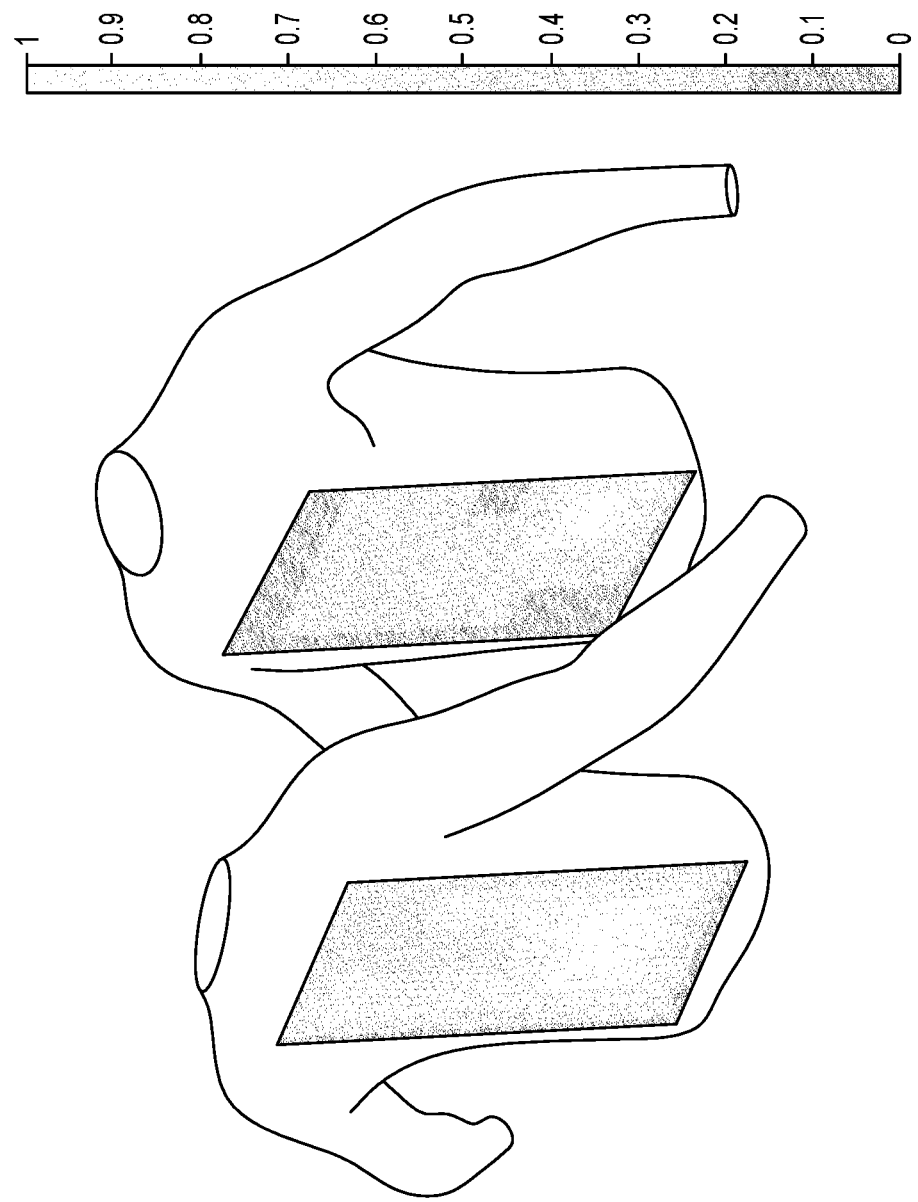
FIG. 14 is a ballistics signal power heat map as measured by the example resistive sensor of FIG. 3 for the front and back of the example garment of FIGS. 2A and 2B.

The rear resistive sensor 14B was placed on twelve (12) different locations on the rear of the garment 12 and for each location, five (5) measurements were taken, each with a duration of 30 seconds, resulting in a total of 150 seconds of data for each location. Then, J-peaks were manually labeled and the average amplitude across all J-peaks was considered as a signal quality factor for each sensor 14, resulting in a 3×4 matrix. The result was then interpolated to achieve higher resolution. A similar procedure was performed for the front resistive sensor 14A on the front of the garment 12 (i.e., twelve locations, five measurements of 30 seconds each for each location). A heat map was generated from the resulting amplitudes for the locations of the front resistive sensor 14A and the rear resistive sensor 14B, which are shown schematically in FIG. 14.

It was observed that the front resistive sensor 14A had superior signal strength compared to the rear resistive sensor 14, especially in the stomach area. Although not wishing to be bound by any theory, the inventors believe that this is because the wearer's spine and rib cage diminish power of heart ballistics. The placement of the triboelectric sensor 16 was also empirically determined. Only one triboelectric sensor 16 was used to reduce the complexity of dealing with too many sensors. While multiple locations may have worked for the triboelectric sensor 16, it was noticed that the worst posture for the resistive sensor 14 was when the wearer was lying on his or her back, particularly when the wearer has high body weight. In this case, the triboelectric sensor 16 could compensate for a poor signal from the resistive sensor 14 since it can provide an accurate heart rate signal even when only a textile (i.e., of the garment 12 and/or a blanket 8) is lying on the wearer's chest. Since a resistive sensor 14 and a triboelectric sensor 16 could not be placed at the same location, in an example, the front resistive sensor 14A was moved to the second-best position, which was the wearer's chest rather than proximate to the wearer's stomach.

Signal Processing of Sensor Outputs

Figure 8A:
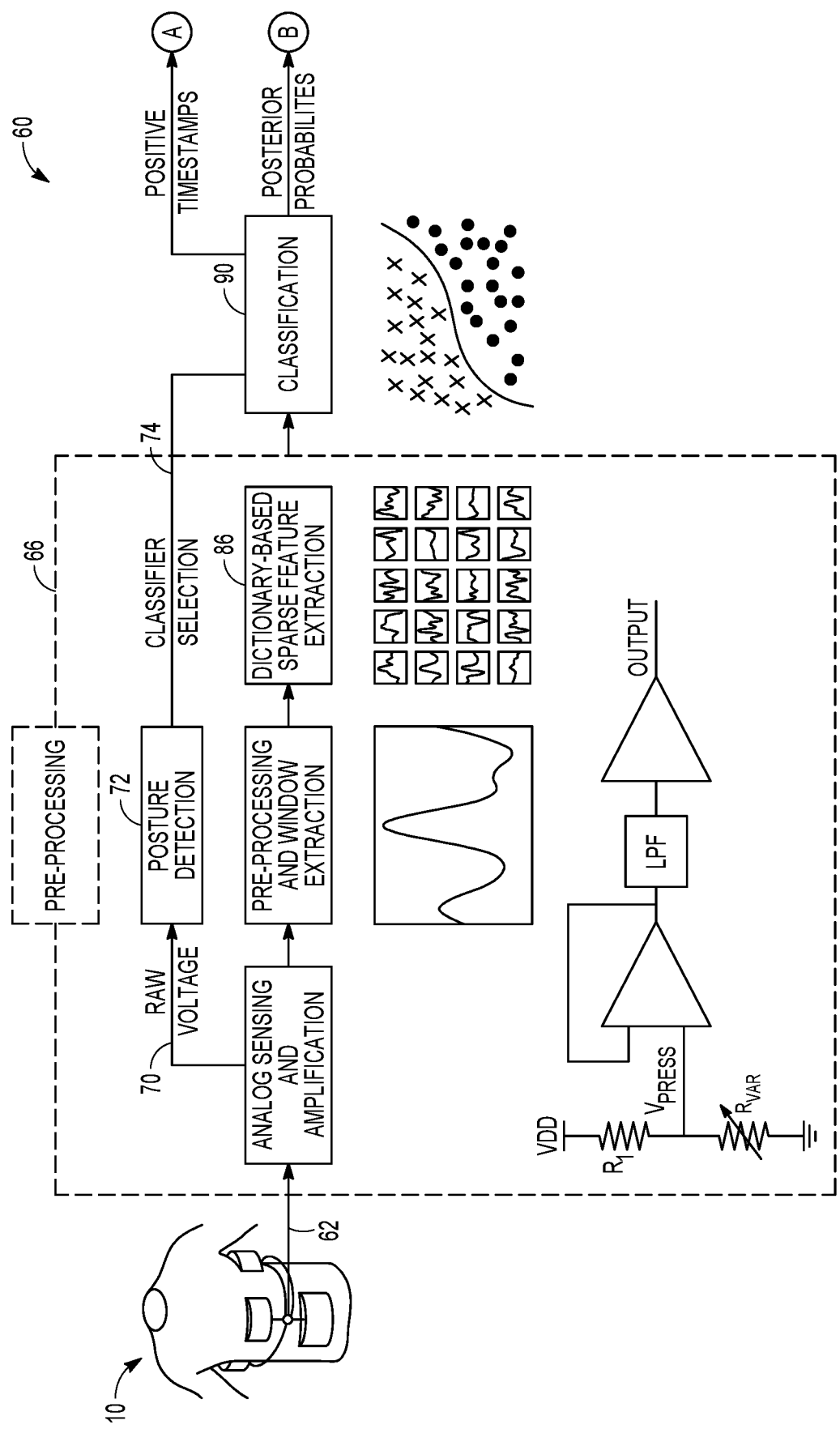
FIGS. 8A and 8B show a flow diagram of an example signal processing pipeline for measuring one or more physiological conditions of the wearer of the example garment of FIGS. 2A and 2B.
Figure 8B:
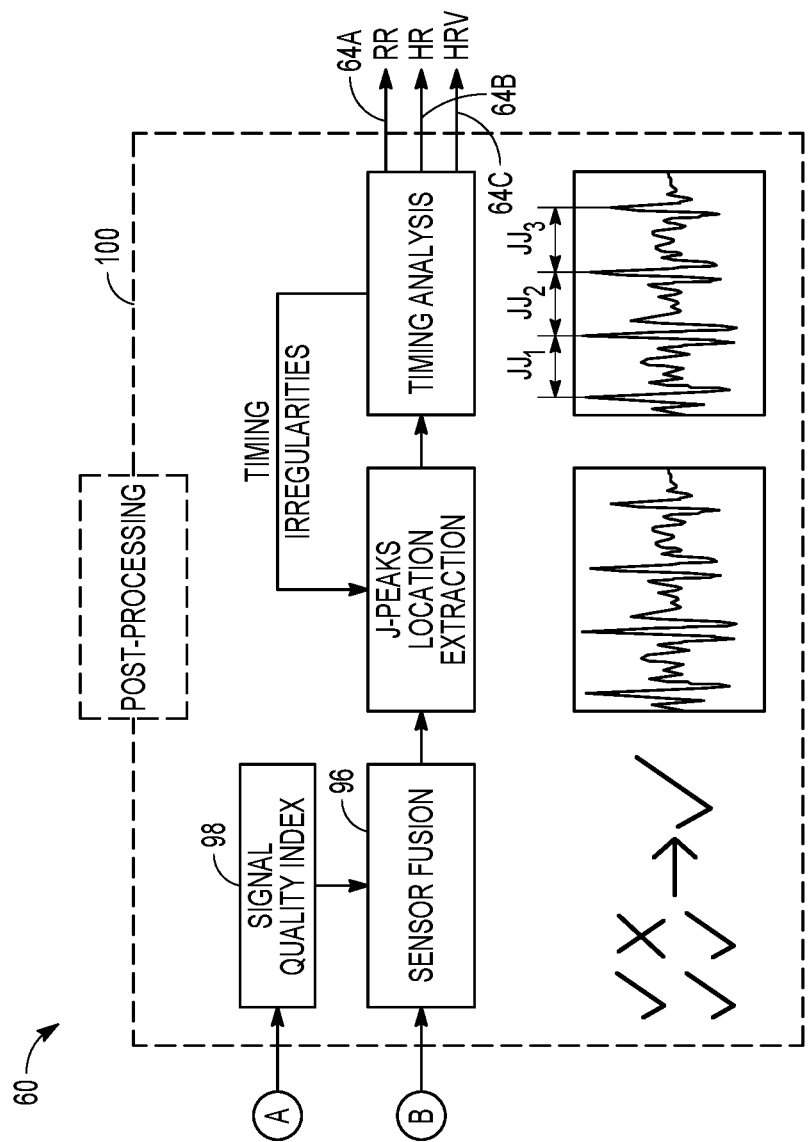

FIGS. 8A and 8B (collectively referred to as "FIG. 8") is a schematic flow diagram of an example algorithm 60 for analyzing output signals 62 from the garment system 10, e.g., signals corresponding to pressure measurements from each of the one or more resistive sensors 14 and ballistic signals from the triboelectric sensor 16. It may help to think of the signal processing algorithm 60 shown in FIG. 8 as a "pipeline" through which the signals pass and are "processed" to provide a final "product," i.e., one or more usable output values 64A, 64B, 64C (collectively "output values 64" or "output value 64") that predictably correspond to one or more physiological conditions of the garment wearer. For this reason, the algorithm 60 of FIG. 8 may also be referred to as "the signal processing pipeline 60" or simply "the pipeline 60."

In an example, the goal of the signal processing pipeline 60 is to provide a comprehensive set of physiological measures of one or more of respiratory and cardiac rhythm including one or more of breathing rate 64A (labeled as "BR 64A" in FIG. 8), heart rate ("HR 64B" in FIG. 8), and heart rate variability ("HRV 64C" in FIG. 8). These physiological parameters are useful for many applications including, but not limited to, sleep stage classification, sleep quality estimation, recovery during endurance training, stress management, and disease prediction. In some examples, the combination of sensors 14, 16 and the signal processing pipeline 60 can determine sleep position in addition to cardiac and respiratory rhythm by leveraging the presence of the several sensors 14, 16 in the garment system 10.

Figure 9B:
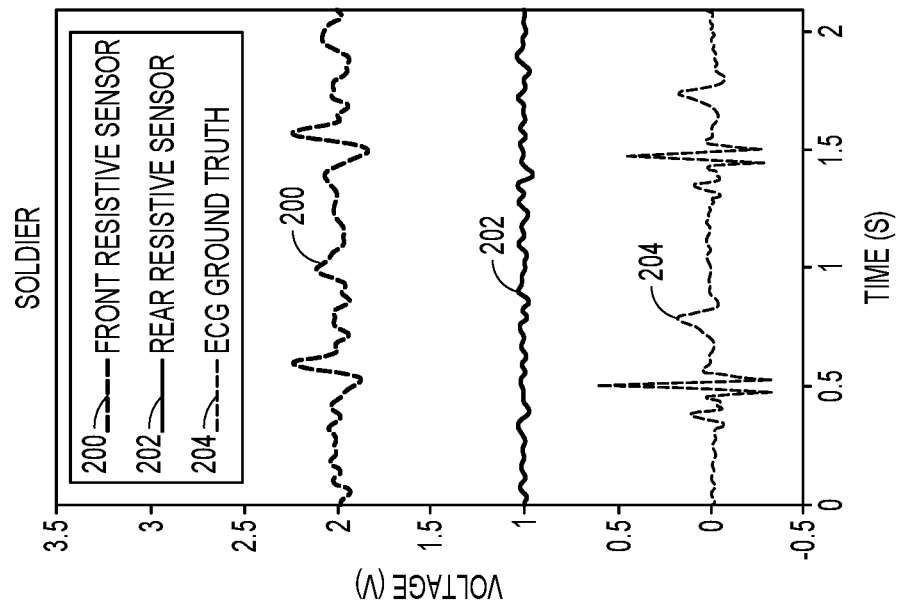
FIG. 9B is a graph showing the voltage response from the first resistive sensor on the chest and the second resistive sensor on the back while the wearer is lying in a prone position.
Figure 9A:
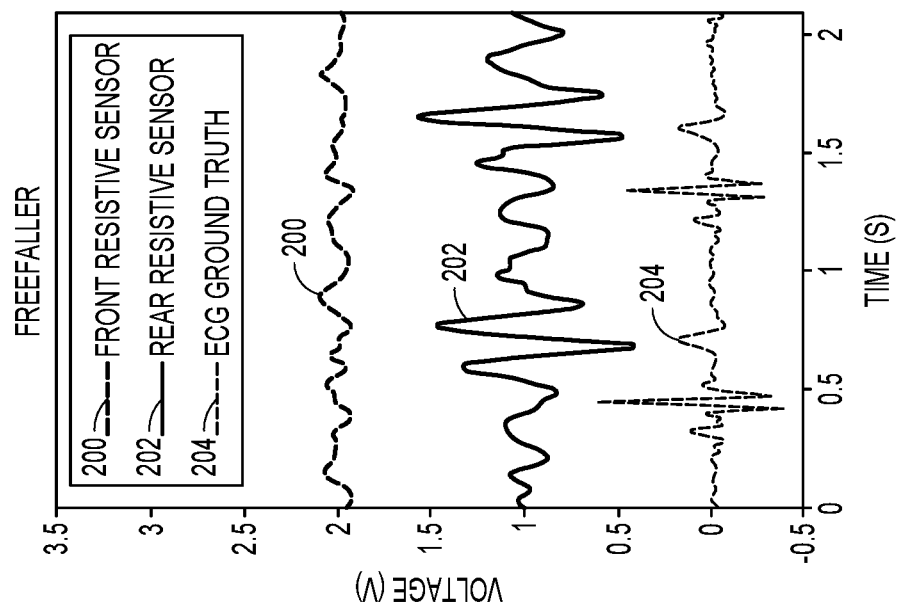
FIG. 9A is a graph showing the voltage response from a first resistive sensor according to FIG. 3 placed on the chest of the example garment of FIGS. 2A and 2B and a second resistive sensor according to FIG. 3 placed on the back of the example garment while the wearer is lying in a supine position.

The central challenge of processing the output signals 62 from the one or more resistive sensors 14 and the triboelectric sensor 16 is that the signals observed by the sensors 14, 16 depend on several factors including the wearer's posture, the wearer's weight, the fit of the garment 12, and the extent of contact between the garment 12 and the wearer's body 2. An example of this difficulty is shown in FIGS. 9A and 9B, which show the signals from the front resistive sensor 14A (data series 200) and from the rear resistive sensor 14B (data series 202) and compares both to the ECG ground truth signal (data series 204). FIG. 9A shows the data when the wearer is laying in a prone (i.e., face down) position, while FIG. 9B shows the data from the sensors when the wearer is lying in a supine (i.e., face up) position. As can be seen from FIGS. 9A and 9B, for both the prone position and the supine position, one of the sensors performs poorly while the other sensor provides a clearer signal. Therefore, it is believed that to best obtain robust physiological measurement under different real-world situations, it will useful to fuse information from different sensors.

Pre-Processing Stage

Returning to FIG. 8, a first stage of the example signal processing pipeline is a signal pre-processing stage 66, also referred to simply as "pre-processing 66." The pre-processing stage 66 acts to filter out various noise sources (to the extent possible). The output voltage 68 is a combination of DC offset generated by amplifiers (e.g., the example amplifier circuit of FIG. 5), low-frequency components corresponding to respiration, higher frequency components corresponding to the BCG signal, and noise in all frequency bins. At the pre-processing stage 66, the DC baseline 70 from each resistive sensor 14 can be directly used to obtain two measures: a) posture based on relative pressure across the sensors; and b) respiration based on baseline pressure variations.

The DC baseline 70 directly provides the pressure for each resistive sensor 14 which, in turn, provides information about the contact between the various sensors 14 and the wearer's body 2. This information can be fused to determine posture at 72. When different DC baseline signals 70 were measured for different postures, it was found that the baseline signals 70 from the resistive sensors 14 are highly distinct. A simple decision tree 74 can very accurately distinguish between different postures. For example, if the front resistive sensor 14A has a high DC baseline 70 and the rear resistive sensor 14B has a low DC baseline, then it can be assumed that the wearer is laying in face-down posture. If the left resistive sensor 14C has a higher DC baseline 70 than the right resistive sensor 14D, than it can be determined that the wearer is leaning toward his or her left side (with the amount of lean being proportional to the amount of the DC baseline for the left resistive sensor 14C as compared to the right resistive sensor 14D).

The DC baseline can also be used to obtain the respiration rate (also sometimes referred to as simply "RR") of the wearer in a straightforward manner. It was determined that the respiration rate of the wearer can be accurately estimated with a two-step sub-process. First, the frequency bin with the highest power is found and is determined to correspond to the respiration signal. Second, band-pass filtering based around the FFT peak is performed to avoid counting fluctuations of the second harmonic. The result of the band-pass filter is a signal oscillating around zero. The number of zero crossings are counted and divided by the duration of the signal to find the duration of a half cycle. Since a respiration measure can be obtained from each resistive sensor 14, the median across all of the resistive sensors 14 (e.g., the front, rear, left, and right resistive sensors 14A, 14B, 14C, and 14D in the example garment system 10 of FIGS. 1A-1C, 2A, and 2B) is determined to obtain an aggregate measure of the wearer's respiration rate.

Determining an accurate measure of heart rate (also referred to herein as "HR") is more challenging, particularly if the goal is to get accurate detection of BCG peaks in order to estimate heart rate variability (also referred to herein as "HRV"). A voltage sample at each resistive sensor 14 in the pre-processing stages 66 is shown in FIG. 10. As can be seen, the respiration signal 80 is quite clear, but the BCG signal 82 is more variable and has many peaks that could be misclassified as heart beats. The rest of the signal processing pipeline 60 is designed to detect individual heartbeats and peak locations.

Heart Rate Processing Via Feature Extraction from Sensors

A BCG signal 82 can be dependent on which type of sensor 14, 16 is being used to determine the signal 82. As described above, each resistive sensor 14 measures pressure changes whereas the triboelectric sensor 16 measures surface charge transfer. Since these are very different types of signals, different feature extraction techniques are used for each sensor 14, 16.

Resistive Sensor

ECG feature extraction has been studied for many decades, applying existing techniques to the extraction of BCG features from the resistive sensor is non-trivial for at least two reasons. First, the BCG signal 80 varies depending on where the sensor 14 touches the wearer's body 2. The reason for this being that the ballistic signal detected by the resistive sensor 14 is impacted by the skeletal structure, particularly the spine. Second, the types of noise in the resistive sensor 14 also differ because motion-induced artifacts like static noise are different across the different locations of the resistive sensors 14. This diversity means that traditional detectors can provide sub-optimal performance when subject to these variations. The signal processing pipeline 60, therefore, uses unsupervised methods for robust feature extraction to deal with a range of signal variation and noise sources observed in the ballistic signal.

In an example, the signal processing pipeline 60 uses sparse coding, which can leverage vast amounts of unlabeled data to generate features. Sparse-coding methods have also been applied to a limited extent in the context of ECG signals and BCG signals. The general concept of sparse coding for physiological waveforms is to extract a dictionary of features 86 for detecting the various peaks (e.g. the P, Q, R, S, and T peaks in the case of an ECG) in a robust manner despite extremely noisy data. In the context of the garment system 10, sparse coding was used to learn a sparse dictionary of shapes of the ballistic signals observed at different locations of the resistive sensors 14 on the garment 12.

Sparse coding is a method for representing a feature vector X in terms of sparse linear combinations $\Sigma_{k=1}^{K} \alpha_k B_k$ of a set of K basis vectors, $B_k$. Given a set of basis vectors $B_k$, the sparse coefficient vector $\alpha_k$ is computed as the solution to the $l_i$ regularized optimization problem of Equation [4].

$$\underset{\alpha}{\mathrm{argmin}} \left\| X_n - \sum_{k=1}^{K} \alpha_k B_k \right\|_2^2 + \lambda \|\alpha\|_1 \quad [4]$$

Figure 11:
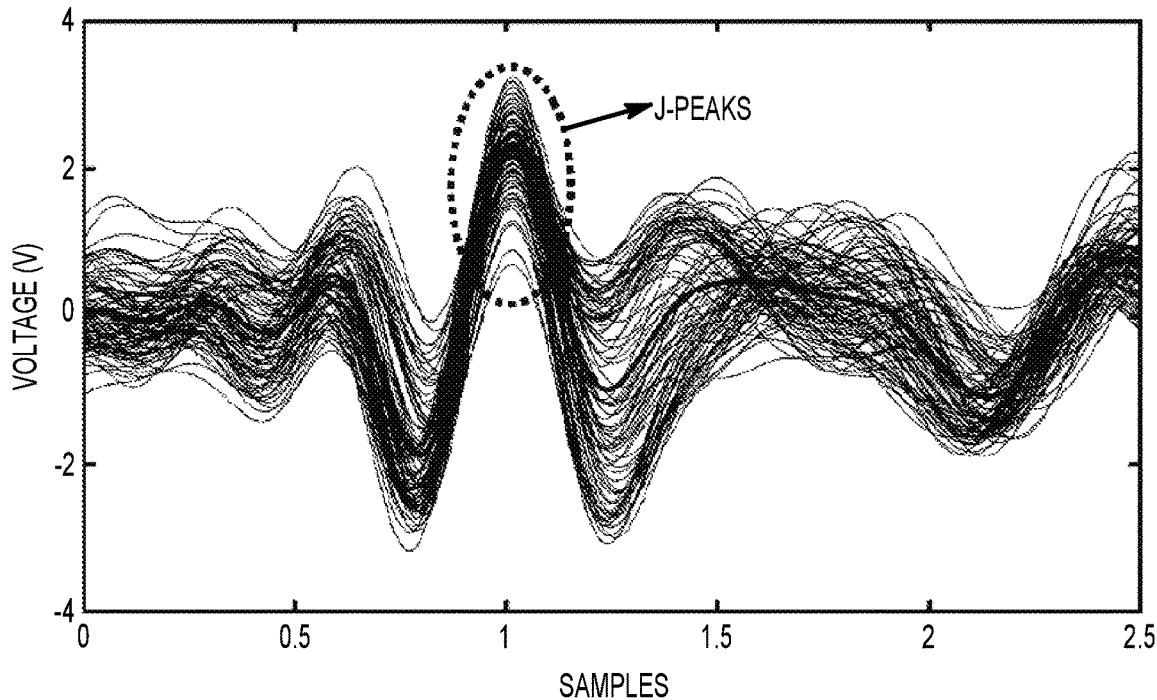
FIG. 11 is a graph comparing multiple traces of BCG signals from the resistive sensor of FIG. 3.

Given a data set $D=\{X_n\}_{n=1:N}$, the basis is learned to minimize errors between each data case and its reconstruction with the constraint of sparse coefficients. The typical approach to solve this is by using an alternate minimization strategy. The goal of the sparse coding of the signal processing pipeline 60 is to determine the highest BCG peak, also known as J-peak, using sparse coding. A peak detector with a fairly relaxed threshold is applied over the signal to over-generate candidate peaks. FIG. 11 shows several instances of such a window overlaid on top of each other for the rear resistive sensor 14B. The BCG waveform observed in FIG. 8 for the garment system 10 is very similar to the pattern presented in literature.

Note that sparse coding can be used to learn an overcomplete basis in a fully unsupervised manner. This is attractive because it means that a new user need not provide labeled data. Rather, the dictionary 86 can simply be expanded by leveraging raw data from a new user. This can provide for the construction of a more representative population-level dictionary 86 without requiring additional labeling overhead for a new user.

Using parameters defined for sparse coding, a dictionary 86 of basis vectors is learned from the time series windows that have been cropped over candidate peaks in a preprocessing and window extraction step 88. As a result, each window can be represented by a series of weights corresponding coefficients for linear combination of dictionary elements to recreate the window. These weights are used as features for the classification stage 90 of the signal processing pipeline 60 of FIG. 8.

Triboelectric Sensor

The signal obtained from the triboelectric sensor 16 is different from the canonical BCG shape that is observed with movement (or other pressure) sensors. In the case of the triboelectric sensor 16, what is being measured is the charge and discharge of the triboelectric materials which approximately corresponds to how it compresses and releases as a consequence of ballistics caused by the wearer's heartbeat (as described above).

Figure 12:
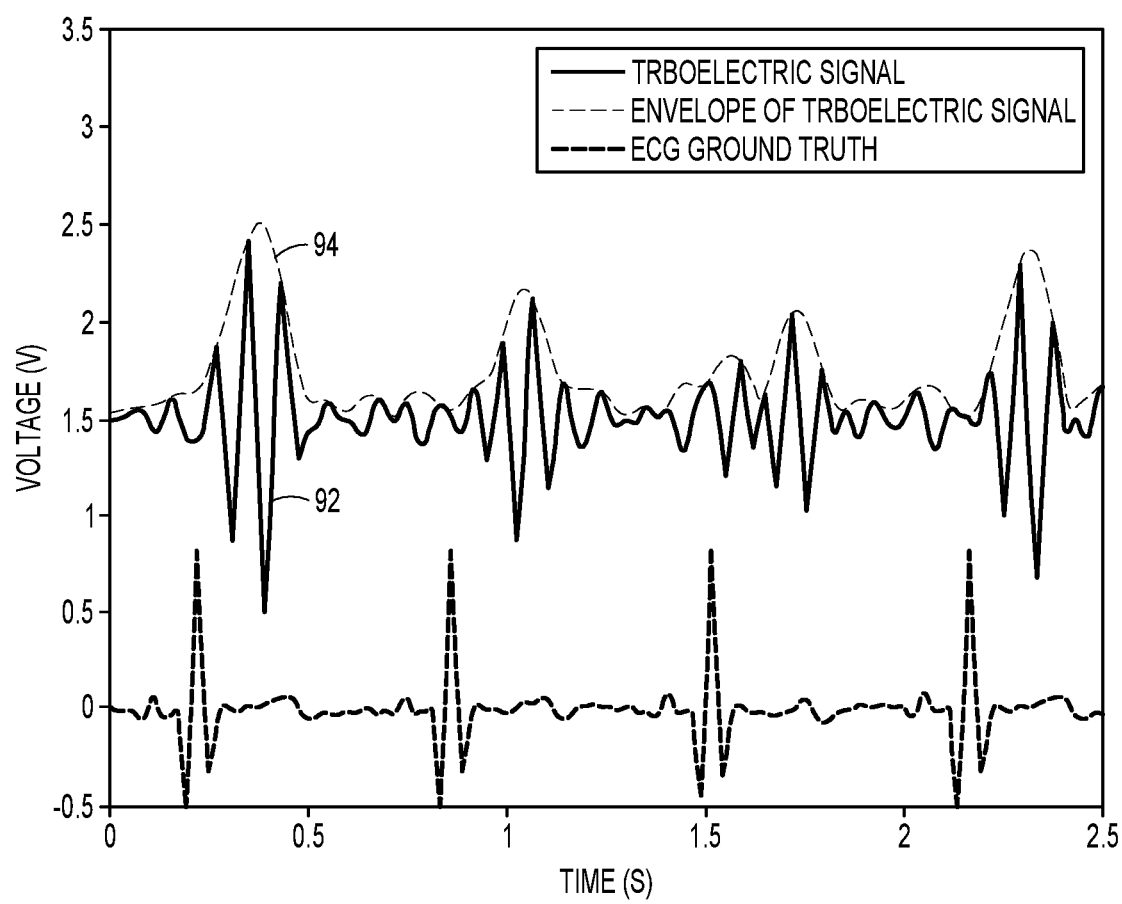
FIG. 12 is a graph comparing the triboelectric behavior of the triboelectric sensor of FIG. 4 compared to the ground truth ECG.

FIG. 12 shows an example of the triboelectric waveform signal 92. As can be seen, the ballistics of the heart causes the triboelectric signal 92 to oscillate much like a spring-mass system with some damping due to the textile properties of the garment 12. FIG. 12 also plots the envelope 94 of the triboelectric signal 92 (also referred to herein as "the triboelectric envelope 94"), with the assumption that the amplitude of the envelope 94 roughly correlates with the amount of mechanical energy on the wearer's skin surface.

In an example, a J-peak based method to extract features from the triboelectric signal 92 was not used because the triboelectric sensor 16 is observing a derived signal that is induced by the ballistics of the heart. Also, the signal peak is variable and unstable since there is relatively weak contact between the triboelectric sensor 16 and the wearer's body 2, at least in the example of the garment system 10 shown in FIGS. 1A-1C, 2A, and 2B where the triboelectric sensor 16 is located on the wearer's stomach where the triboelectric signal 92 is impacted by posture and how the textile 12 rests against the wearer's body 2.

For this reason, in some examples, instead of using an analysis of the peaks of the triboelectric signal 92, the signal processing pipeline 60 can use the triboelectric envelope 94 as the source of features. The triboelectric envelope 94 loses information about the location of the peaks but is more robust to outliers. After determining the triboelectric envelope 94, the inventors have found that typically there is a correlation between the locations of peaks of the triboelectric envelope 94 and the expected location of a J-peak. Using this insight, in an example, multiple samples can be taken from the triboelectric sensor 16 over a regular interval and those values can be used as triboelectric features for classification. In one example, five (5) samples of the triboelectric envelope 94 were taken with a 100-millisecond interval and were used to determine the triboelectric features.

J-Peak Classification

The next stage of the signal processing pipeline 60 classifies the candidate peaks into valid or invalid BCG J-peaks. This stage is executed on a per-sensor basis, i.e., the peaks for each sensor are classified separately in this stage and are then fused in subsequent stages.

To perform J-peak classification, the first step is to collect labeled data using an ECG sensor as ground truth. Depending on placement of each textile-based sensor, the BCG J-peak will have a small delay relative to its corresponding ECG R-peak. This delay is called the RJ duration and is affected by many factors including an individual's medical condition and placement of the sensor. This duration can reach up to 300 milliseconds. To account for this delay, the largest peak that appears within a 400 ms window after an ECG R-peak is labeled as the BCG J-peak. Then, a few cases per sensor were manually checked to validate the labeling of the BCG J-peak.

In an example, the signal processing pipeline 60 uses five (5) sets of features for the classifiers: (1) the sparse coding feature weights corresponding to the dictionary (determined as described above), (2) posture information coming from the DC baseline 70, (3) amplitude of the peak, (4) the multiple samples from the triboelectric envelope 94 centered around the peak, and (5) multiple samples from the envelope of the resistive sensor 14 centered around the peak. In an example, these features are used to classify each candidate peak.

Once the features are determined, the classification model 90 can be any simple machine learning model. In an example, a linear support-vector machine ("SVM") was used as the classification model 90. However, those having ordinary skill in the art will appreciate that other models may be equally viable. The classifier model 90 is trained based on sparse coding weights and other time-domain features described herein and the labels provided for each candidate peak. At this stage, a classification score can also be determined for the classification for each peak. In an example, the classification score is the signed distance from the SVM decision boundary. In an example, the classification score can be used in the fusion stage (described below) to combine the data from multiple sensor streams and improve the overall results.

Multi-Sensor Fusion Stage

Next, the signal processing pipeline 60 enters a fusion stage 96, which fuses the outputs of the individual per-sensor classifiers to determine the location of each J-peak in a more accurate manner. The fusion stage 96 is part of an overall post-processing phase 100 of the signal processing pipeline 60.

In an example, the fusion stage 96 includes determining an estimate of the quality of the measurements from each sensor 14, 16. In an example, this is done by first defining a signal quality index 98 that seeks to identify which sensors provide the most relevant information so that more weight can be assigned to the output from these sensors. In an example, the signal quality index 98 is based on the observation that a poor-quality sensor generally has high variance in the inter-peak intervals since it has more false positives and false negatives. In an example, the signal quality index 98 (SQI) is defined by Equation [5].

$$SQI_{p,u,s} = 1/\text{std}(II_{p,u,s}) \quad [5]$$

where $II_{p,u,s}$ refers to an array of inter-beat intervals for each measurement on user u, in position p, and from sensors. Each element of this array is calculated as the duration between two corresponding consecutive peaks classified as correct J-peaks, as shown in Equation [6].

$$II_{p,u,s} = T_{p,u,s}{}^j(i) - T_{p,u,s}{}^j(i-1) \quad [6]$$

Given the signal quality index 98 per sensor and classification score for each peak from the SVM classifier, a score for each peak, i, is defined as the weighted sum across all sensors. In other words, the scores are summed up the across the different sensors that detect the same peak (within a short time window of each to adjust for timing differences), as in Equation [7].

$$\text{Fused Score}(i) = \sum_{x=1\ldots4} \text{Score}(s) * SQI(s) \quad (7)$$

Next, the peaks that have positive scores after the sensor fusion 96 are selected as the detected J-peaks. There may still be some stragglers that have been missed by this assumption, therefore, another sweep of the resulting inter-beat intervals is performed. For cases where heart rate variance (HRV) exceeds possible range for humans, another peak with the second highest fused score is selected and is added to the detection. At this point, estimated locations of the J-peaks are used in order to calculate the physiological parameters, specifically heart rate (HR) and heart rate variation (HRV).

Figure 13C:
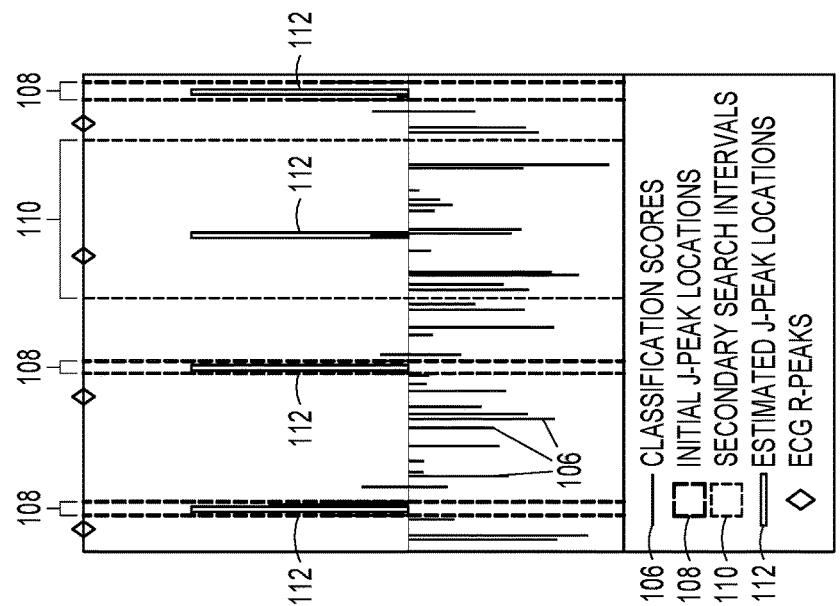
FIG. 13A-13C show graphs of the steps taken to estimate the location of BCG J-peaks for the signals from the resistive sensor of FIG. 3.
Figure 13B:
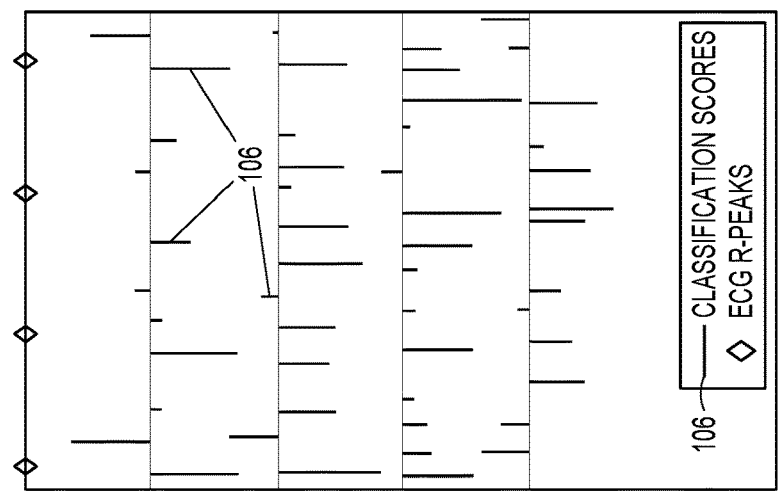
Figure 13A:
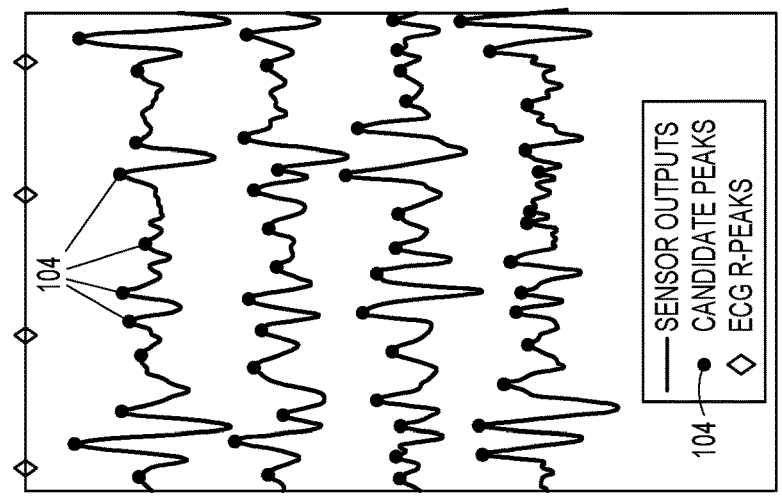

An example of the overall process is illustrated in FIGS. 13A-13C. In FIG. 13A, the over-generated candidate peaks 104 are determined, each of which is classified by the per-sensor classifier. In FIG. 13B, classification scores 106 for each of the peaks is shown. As can be seen in FIG. 13B, only a small number of the candidate peaks 104 have a positive peak score 106. FIG. 13C shows the fusion stages using the aggregated scores across sensors. In FIG. 13C, the smaller regions 108 represent J-peaks that are detected first since the fused score is positive, and the larger region 110 is a secondary search stage where the next highest score is selected to fill a missing peak. The regions 108, 110 are used to determine estimated J-peak locations 112.

Performance Study

User studies were conducted to evaluate and validate the performance of the garment system 10.

Study Participants

The user study included 21 participants ranging in age from 22 to 38 years. Nine (9) of the participants were female and twelve (12) were male. The participants varied in weight from about 107 pounds (about 48.5 kg) to about 240 pounds (about 109 kg), and in height from about 61 inches, i.e., 5 feet and 1 inch (about 155 cm) to about 76 inches, i.e., 6 feet and 4 inches (about 193 cm).

The participants wore an example of the garment system 10 in various stationary conditions and the output voltage was recorded. The example garment system 10 was made with a garment 12 that was a typical extra-large (XL) sized pajama shirt. However, the participants were not restricted solely to this size because many users select sleepwear that is larger than their normal size. Also, even if a participant would normally wear an XL sized shirt, due to variance in sizing amongst different manufacturers garments rarely fit exactly to an individual's size.

Participants were separated into two (2) groups when analyzing the data. The first group included participants for whom the XL sized garment 12 fits relatively well, and the second group included those participants who are generally too short to wear the XL sized garment 12. For the sake of brevity, the first group of participants are referred to hereinafter as "height matched" participants and the second group or participants are referred to hereinafter as "height unmatched," respectively. The height matched participants included eleven (11) of the participants who ranged in height from about 67 inches (about 170 cm) to about 76 inches (about 193 cm). The height unmatched participants included the remaining ten (10) participants with a height below 67 inches (about 170 cm). The group of height unmatched participants varied quite a bit in body type and included both relatively short and relatively thin individuals (in a couple of instances, the garment shirt reached just above the participant's knee). In short, the participants were able to measure performance of the garment system 10 across various dimensions.

Data Collection Methods

Figure 15A:
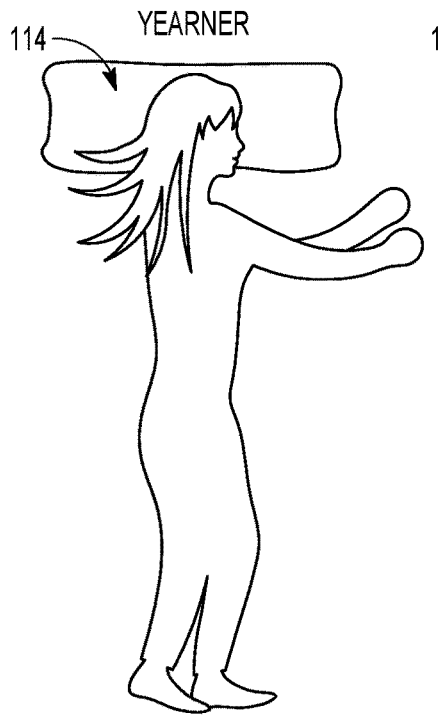
FIGS. 15A-15F are pictures of several common sleeping positions.
Figure 15B:
Figure 15C:
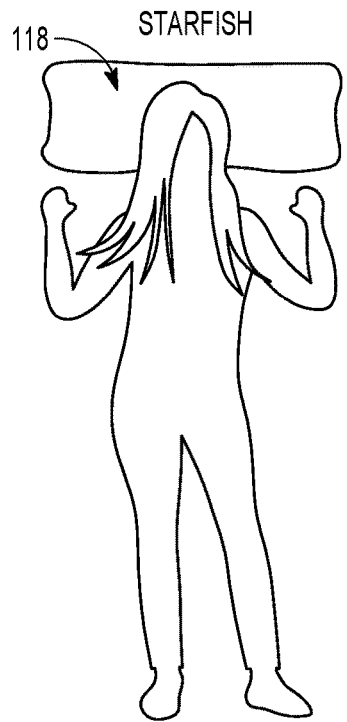
Figure 15D:
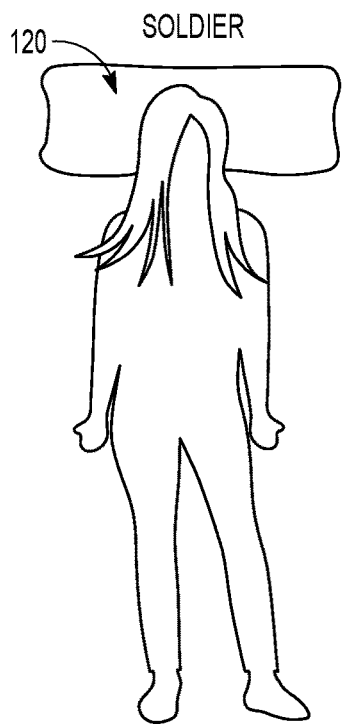
Figure 15E:
Figure 15F:
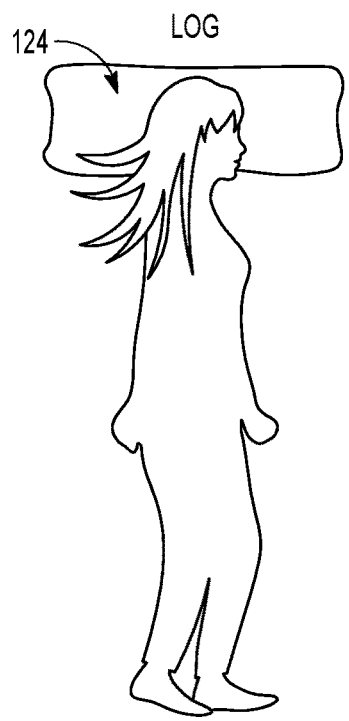

Data was collected in a variety of postures. In particular, because one known application for the garment system 10 is sleep sensing, the study focused on measurement when the participants were in sleep postures. The sleeping postures that were studied are widely classified into six categories as shown in FIGS. 15A-15F. FIG. 15A shows a first sleep posture 114 where the participant is lying on his or her side with arms extend to the side and legs extended down, also referred to herein the "yearner posture 114." FIG. 15B shows a second sleep posture 116 where the participant is lying in a prone or face down posture, also referred to herein as the "freefaller posture 116." FIG. 15C shows a third sleep posture 118 where the participant is lying in a supine or face up with his or her arms extended in the superior direction (e.g., toward the head) at least partially, also referred to herein as the "starfish posture 118." FIG. 15D shows a fourth sleep posture 120 where the participant is lying in a supine or face up posture with his or her arms extended in the inferior direction (e.g., toward the feet), also referred to herein as the "soldier posture 120." FIG. 15E shows a fifth sleep posture 122 where the participant is lying on his or her side with the arms and legs partially tucked, also referred to herein as the "fetal posture 122." FIG. 15F shows a sixth sleep posture 124 where the participant is lying on his or her side with the arms and legs both extended straight or substantially straight in the inferior direction (e.g., toward the feet), also referred to as the "log posture 124." Data was collected from participants in each of the sleep postures 114-124 shown in FIGS. 15A-15F. In addition to the sleep postures 114-124, performance was also evaluated with participants sitting on a chair (e.g., as shown in FIG. 1B) and standing (e.g., as shown in FIG. 1C) as two additional postures of interest since they provide a contrast against sleep postures. In particular, standing represents a difficult scenario because there is minimal pressure against an external surface on which the resistive sensors 14 can rely. Collectively, the six (6) sleep postures 114-124, the sitting posture of FIG. 1B, and the standing posture of FIG. 1C are hereinafter referred to as the "tested postures" for the sake of brevity.

The duration of each measurement for each of the tested postures was for one (1) minute, for a total of eight (8) minutes of recording from each individual participant. Each recording included five channels, four (4) corresponding to each of the resistive sensors and one (1) corresponding to the triboelectric sensor. Since the garment system 10 is designed to measure vital signs, a ground truth for the physiological signals was also recorded. For heart rate, an ECG signal was used as a reference for heartbeats, and a photoplethysmography (PPG) sensor for tracking respiration.

Resistive Sensor Benchmarks

Various aspects of the resistive sensor 14 were benchmarked, as described below.

Pressure Sensitivity

Figure 16:
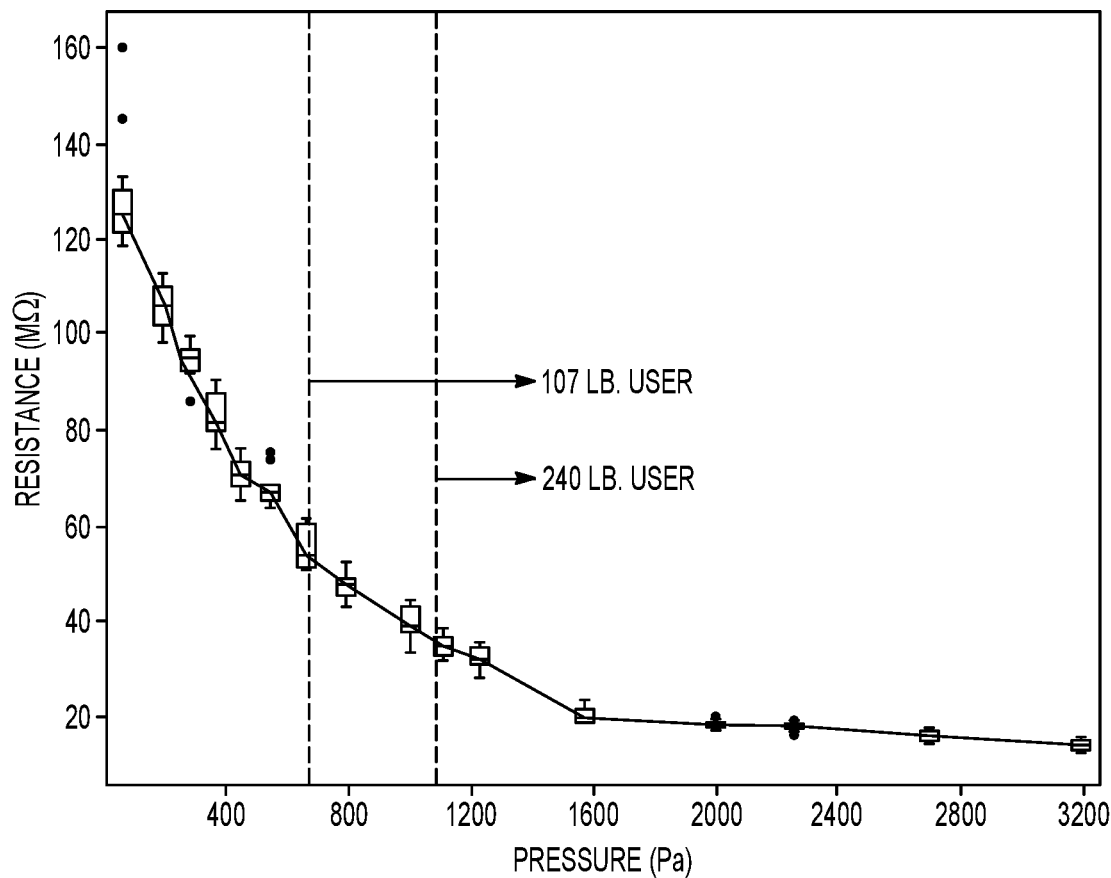
FIG. 16 is a graph showing the voltage signal from all the resistive sensors on the example garment of FIGS. 2A and 2B as the wearer changes from the supine position of FIG. 15D to the fetal position of FIG. 15E and then to the prone position of FIG. 15B.

An experiment was run to validate that the resistive sensor 14 is sensitive to a typical range of pressures experienced by and caused by human interaction. In the experiment, the pressure applied to the resistive sensor (with dimensions of 1.5 inches×2.7 inches, or about 4.05 square inches ($in^2$)) was changed in a controlled manner and the resulting resistance of the resistive sensor 14 was measured. The measurement was repeated ten (10) times for each pressure point by re-applying the pressure in various rotational directions and placements to account for probable folds, asymmetry in functionalization and pressure distribution. FIG. 16 shows a box plot of the changes in resistance for the resistive sensors 14 as a function of the pressure applied to one side of the sensor 14.

As can be seen in FIG. 16, the fabric resistance varies monotonically as the amount of pressure applied to the resistive sensor 14B is increased. The sensitivity of the resistive sensor 14 is inversely related to the amount of pressure applied on the fabric surface of the garment 12. As a reference, FIG. 16 also includes lines 126 and 128, which corresponds to the pressure applied onto the rear resistive sensor 14B by participants weighing about 107 pounds (about 48.5 kg) and about 240 pounds (about 108.9 kg), respectively, when the participants are lying supine (face up). The data of FIG. 16 shows that the resistive sensors 14 are slightly more sensitive to lighter individuals and less sensitive to heavier individuals. However, overall the results show that the resistive sensors 14 have good sensitivity in the typical regime of human weight.

Determining Posture Through Pressure Measurements

Figure 17:
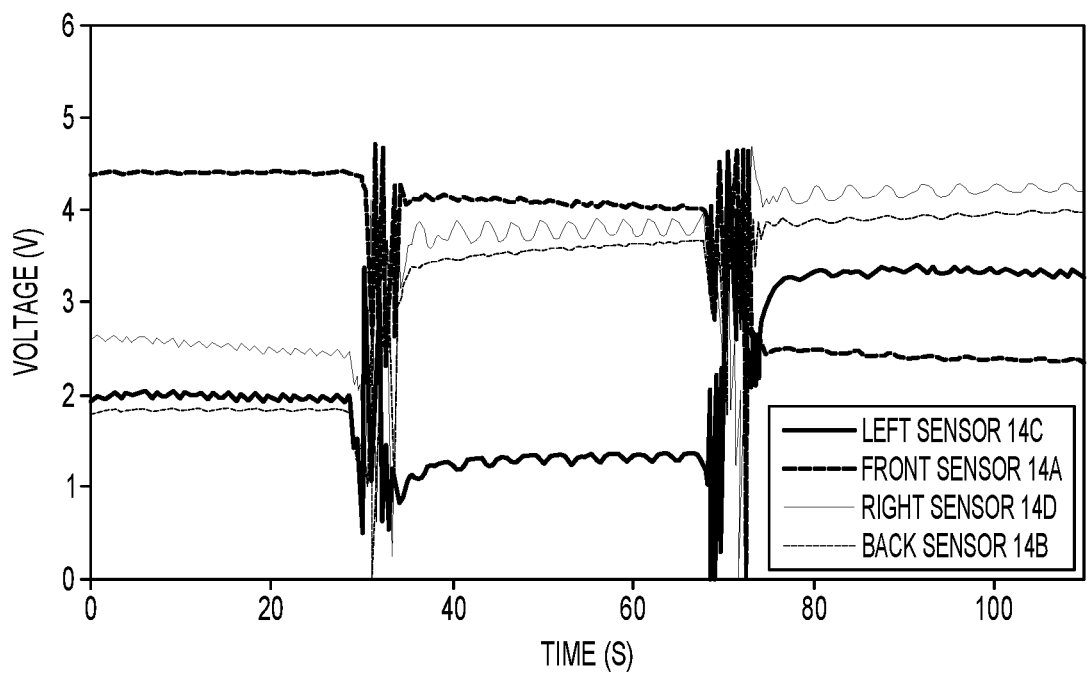
FIG. 17 is a graph of the change in fabric resistance as a function of the pressure applied on one side of the example garment of FIGS. 2A and 2B.

When used in conjunction, the distributed set of resistive sensors 14 can provide very accurate information about posture. FIG. 17 is a graph showing how the pressure baseline (e.g., the $V_{Press}$ signal in FIG. 5) for each of the resistive sensors 14A, 14B, 14C, and 14D changes as the wearer of the garment system 12 transitions between different postures. Specifically, FIG. 17 shows the pressure baseline change as the wearer transitions, at about 30 seconds, from the soldier posture 120 of FIG. 15D to the fetal posture 122 of FIG. 15E and then, at about 70 seconds, from the fetal posture 122 of FIG. 15E to the prone or freefaller posture 116 of FIG. 15B and vice versa. Note that the voltage being measured via the example voltage divider circuit shown in FIG. 5 is inversely proportional to the pressure, so lower voltage means higher pressure. As can be seen by FIG. 17, the resistive sensors 14 that are under pressure have reduced resistance and show lower voltage allowing the resistive sensors 14 to reliably measure pressure.

FIG. 17 shows clear trends. In the supine soldier posture 120 (FIG. 15D), which occurred from 0 seconds to about 30 seconds, the rear resistive sensor 14B has the lowest voltage and the front resistive sensor 14A has the highest voltage. The left resistive sensor 14C and the right resistive sensor 14D that measure arm pressure are less clear indicators of the posture in the case of the supine soldier posture 120. When the subject transitions to the fetal posture 122 (FIG. 15E) at about 30 seconds, the left resistive sensor 14C becomes pressured because the participants were instructed to lie on their left side when in the fetal posture 122, whereas the front resistive sensor 14A, the rear resistive sensor 14B, and the right resistive sensor 14D are not under much pressure. Finally, in the prone or freefaller posture 116 (FIG. 15B), the front resistive sensor 14A sees the highest pressure (as would be expected), while the rear resistive sensor 14B shows a much lower pressure (as would be expected). Thus, posture-dependent changes in pressure detected by the resistive sensors 14 are clearly observable. In an example, a simple decision tree that looks for differences between the front resistive sensor 14A and the rear resistive sensor 14B and/or between the front resistive sensor 14A and the left and right resistive sensors 14C and 14D and/or between the rear resistive sensor 14B and the left and right resistive sensors 14C and 14D can easily identify posture with near 100% accuracy across all wearers of the garment system 10. It is even possible to differentiate between similar postures, such as between the two supine postures (i.e., the starfish posture 118 and the soldier posture 120) due to differences in pressure for the left and right resistive sensors or between the side-lying postures (i.e., the fetal posture 122, the yearner posture 114, and the log posture 124) due to differences in pressure for the front and rear resistive sensors 14A and 14B and the left and right resistive sensors 14C and 14D, as will be appreciated by those of skill in the art.

Measuring Physiological Parameters

The performance of the garment system 10 in detecting and measuring physiological variables of interest—including, but not necessarily limited to, respiration rate, heart rate, and heart rate variability. For the validation study, "heart rate variability" or "HRV" refers to root-mean square differences of successive R-R intervals (hereinafter "RMSSD"), which is a common measure of HRV. These physiological variables are determined according to the signal processing blocks described above with respect to the signal processing pipeline 60 of FIG. 8.

Figure 18:
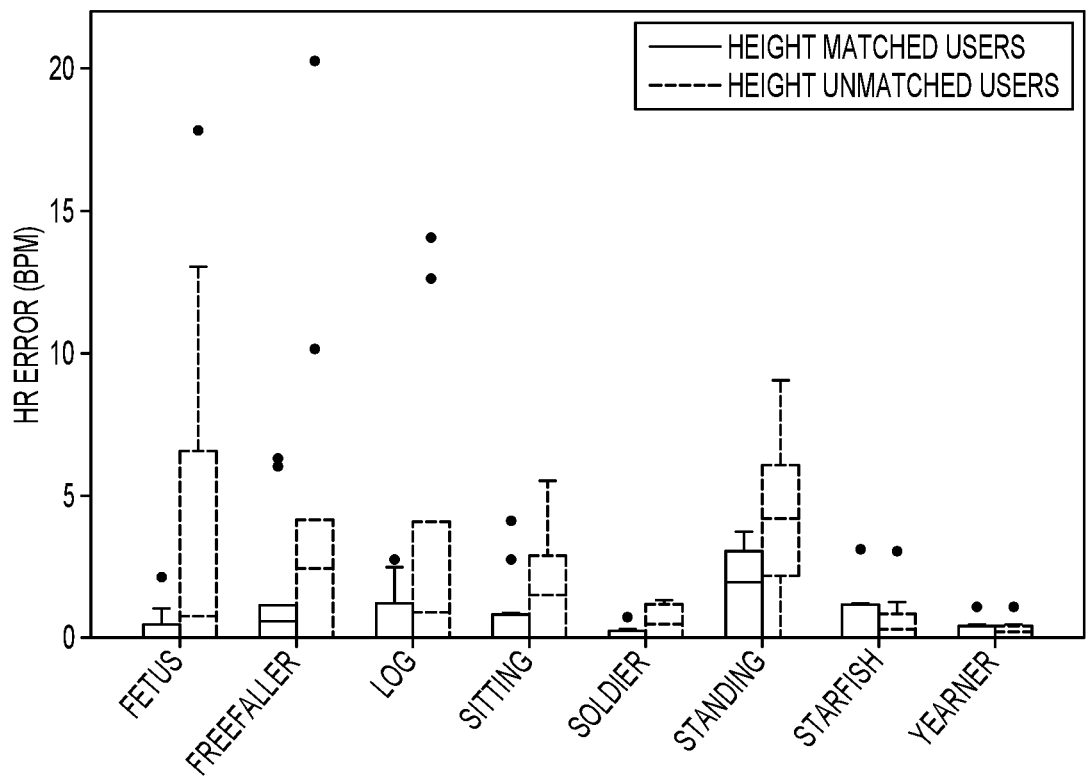
FIG. 18 is a graph showing the error for the heart rate measured by the example garment of FIGS. 2A and 2B in various positions.
Figure 19:
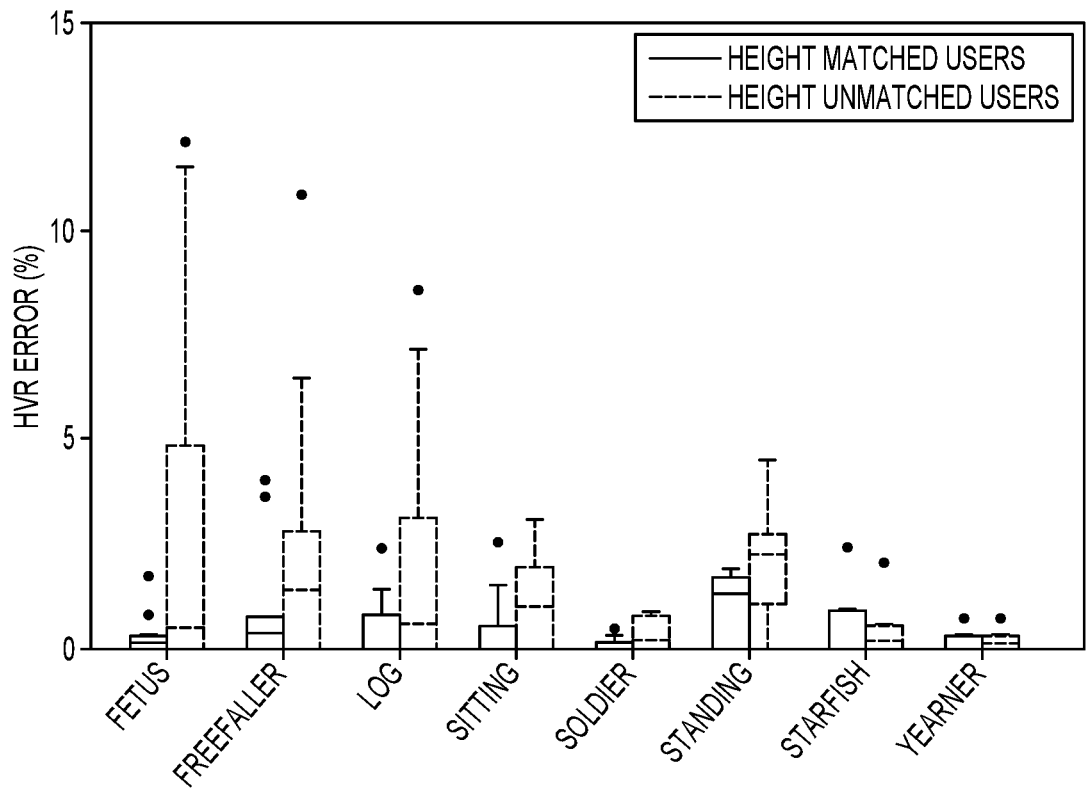
FIG. 19 is a graph showing the error for heart rate variability (HRV) measured by the example garment of FIGS. 2A and 2B in various positions.
Figure 20:
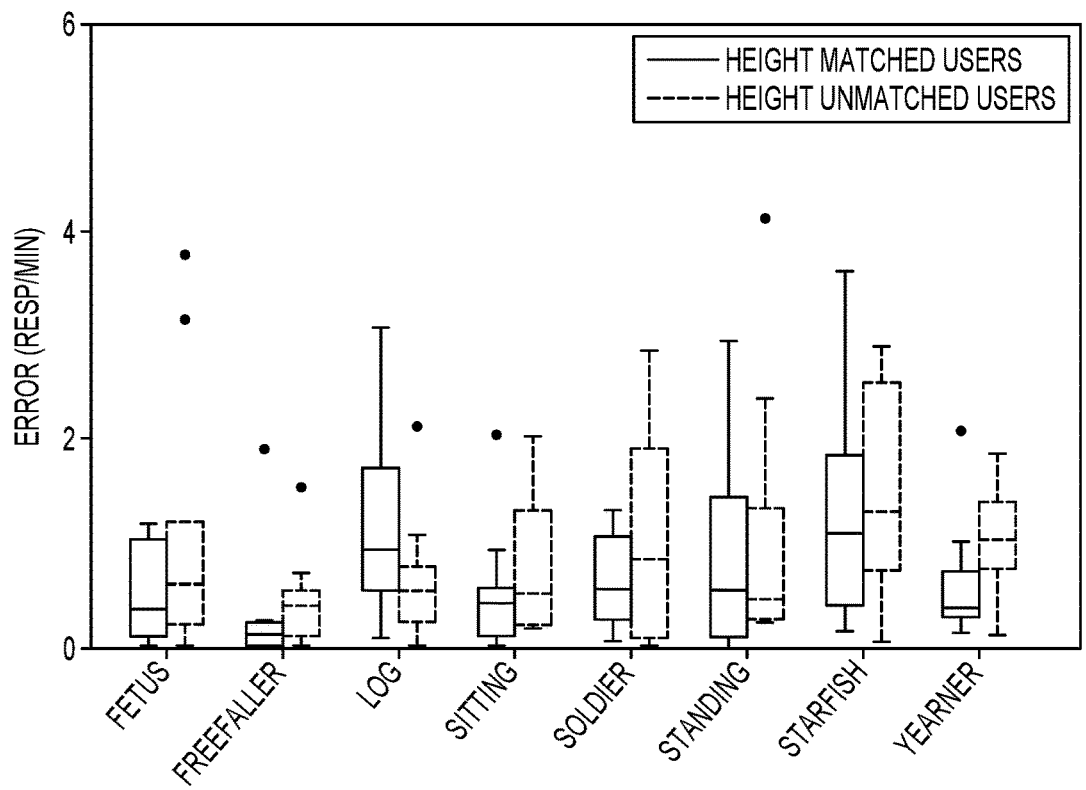
FIG. 20 is a graph showing the error for breathing rate measured by the example garment of FIGS. 2A and 2B in various positions.

FIGS. 18-20 show the performance of the garment system 10 in measuring heart rate (also referred to as "HR"), HRV, and respiration rate (also referred to as "RR"). FIG. 18 shows the error in estimating HR by the garment system 10 in each of the eight (8) tested postures (i.e., sitting (FIG. 1B), standing (FIG. 1C), yearner posture 114 (FIG. 15A), freefaller posture 116 (FIG. 15B), starfish posture 118 (FIG. 15C), soldier posture 120 (FIG. 15D), fetal posture 122 (FIG. 15E), and log posture 124 (FIG. 15F)). FIG. 19 shows the error in estimating HRV in each of the tested postures. FIG. 20 shows the error in estimating RR in each of the tested postures. Each of FIGS. 18-20 also split the data between the height matched group and the height unmatched group.

FIGS. 18-20 show results that are very good across all three physiological parameters. When measuring heart rate, for the height-matched participants error in HR estimation was generally less than 1 beat per minute ("bpm") and error in HRV estimation was less than 0.5%. The only posture that had relatively high error was the standing posture (FIG. 1C), which is to be expected because there is no externally pressured surface beyond typical atmospheric pressure to act on the resistance sensors 14, so the garment system 10 must rely on weaker signals from the pressure of the arm against the torso for the left and right resistive sensors 14C and 14D and the triboelectric sensor 16 resting on the wearer's stomach. But even in the standing case, the error is not too high, e.g., the median HR error was about 2.5 bpm and median HRV error was about 2%. For the height unmatched participants, the upper quartile and worst-case error is more but the median error is only a little more than then height-matched case (roughly 2 bpm for the HR error and 2% for the HRV error). In all cases, the results are better for the height-matched participants compared to the height-unmatched participants.

The respiration metrics were also very good. The median error was generally below 1 respiration per minute ("resp/min"). The error was higher for the starfish posture 118 and the soldier posture 120. Without wishing to be bound by any theory, the inventors believe this was so because the rear resistive sensor 14B saw a weaker respiration signal due to the wearer's spine, and because the triboelectric sensor 16 on the stomach did not help since it cannot measure slow baseline changes (which is the case with respiration). The signal in these postures 118 and 120 are primarily from the front resistive sensor 14A on the chest and sensor fusion is less useful in these postures 118, 120 leading to higher error.

Performance of Signal Processing Pipeline

Having discussed the application-level benchmark metrics, the performance of the garment system 10 was also evaluated for each block of the signal processing pipeline 60 of FIG. 8. First, the evaluation looked at the overall results for J-peak detection via the entire pipeline 60. Then various stages in the signal processing pipeline 60 were compared to see their effect in overall accuracy.

J-Peak Detection

The effectiveness of distinguishing J-peaks amongst all candidate peaks by the signal processing pipeline 60 was evaluated. $F_1$-score was used as a measure of performance of the classification 90, which was performed using Leave-One-Subject-Out (LOSO). In this result, the height-matched participants were not distinguished from the height-unmatched participants, and instead the process aggregated results for all participants.

Table 1 below lists the $F_1$ scores from each of the resistive sensors 14 in each of the tested postures (sitting, standing, and the sleep postures 114-124) as determined from the classification stage 90 of the signal processing pipeline 60 of FIG. 8, prior to fusion 96 of the data in the post-processing stage 100. As can be seen in Table 1, there is substantial variation in the results and the scores are relatively poor for some individual sensors 14. For example, the rear resistive sensor 14B can have poor performance when there is too much pressure on it (such as in the starfish posture 118) or when there is little to no pressure at all (such as in the fetal posture 122). However, the rear resistive sensor 14B offers very good performance in some other positions (e.g., the freefaller posture 116 and when standing). Similarly, each resistive sensor 14 performs better in some scenarios and worse in others. Also, it is important to note that no single resistive sensor 14 received an $F_1$ score above 90%. Rather, in most cases, it hovers between about 75% and about 80%.

TABLE 1

Median $F_1$ Score Before Fusion

| Posture | Resistive Sensor | | | |
| --- | --- | --- | --- | --- |
| | Front (14A) | Rear (14B) | Left (14C) | Right (14D) |
| Fetal | 66.1 | 43.0 | 71.8 | 68.4 |
| Freefaller | 776.6 | 80.9 | 79.4 | 75.7 |
| Log | 70.1 | 44.8 | 67.2 | 76.7 |
| Sitting | 71.0 | 66.2 | 75.3 | 65.7 |
| Soldier | 61.9 | 62.6 | 82.2 | 88.4 |
| e | 68.4 | 78.0 | 81.4 | 78.2 |
| Starfish | 84.2 | 40.0 | 73.4 | 79.7 |
| Yearner | 69.9 | 64.5 | 74.8 | 73.8 |

Figure 21:
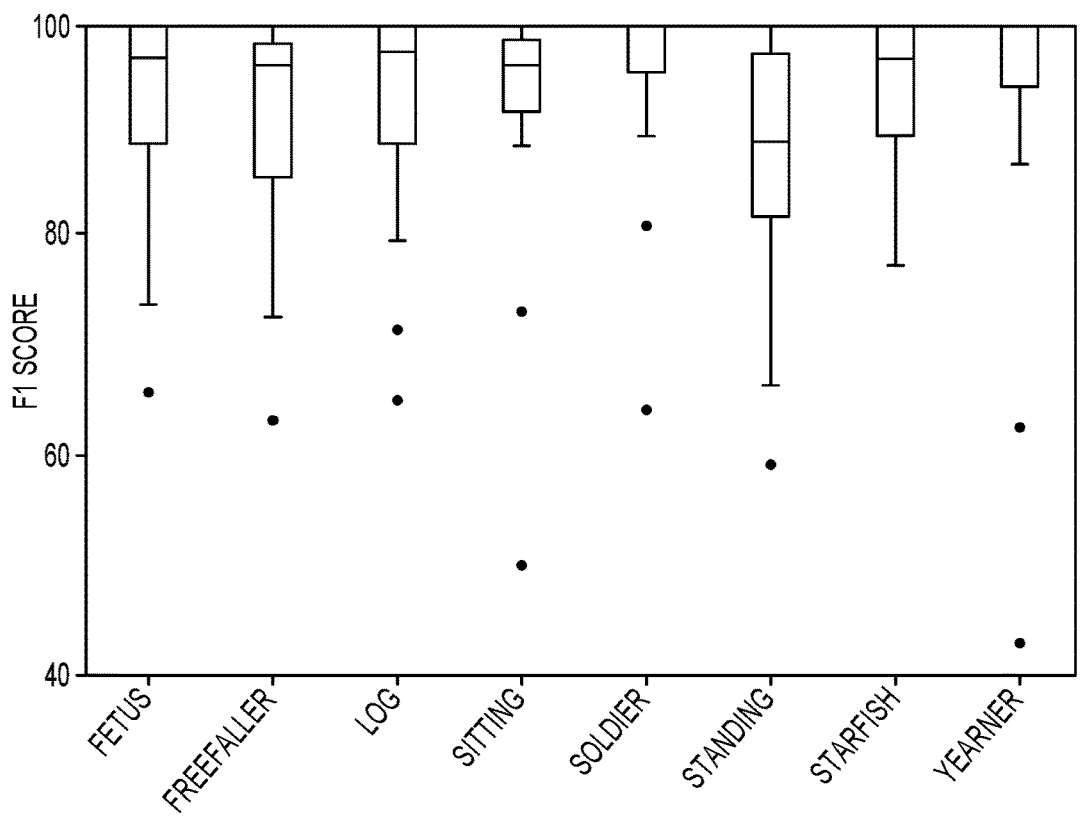
FIG. 21 is a graph of the $F_1$ score for the data measured by the example garment of FIGS. 2A and 2B after fusion in the example signal processing pipeline of FIG. 8.

FIG. 21 is a bar graph showing the $F_1$ score for each of the tested postures after fusion 96 of the data in the post-processing stage 100 of the signal processing pipeline 60. As can be seen in FIG. 21, the $F_1$ scores after fusion 96 are considerably higher, and the median $F_1$ score was often close to 100% and was above 95% for almost all the tested postures. The highest error was for the standing posture, and it is believed that this can be accounted for due to reasons discussed above. The upper quartiles have somewhat higher error—this is primarily because of the height-unmatched participants whose error was higher than the height-matched participants.

Error Contribution Breakdown

A breakdown of the error contributions of various aspects of the garment system 10 and the signal processing pipeline 60 is discussed below.

Signal Processing Pipeline Stage Contribution

For this breakdown measure, results were analyzed by selectively choosing blocks of the signal processing pipeline 60 and measuring the accuracy of the garment system 10. In this breakdown, three different signal processing algorithms were considered. The first algorithm corresponds to the best-case performance when a single sensor was used, which is defined as the best sensor for each participant and posture for these numbers, i.e., the error that results after the classification step 90 but before the sensor fusion 96 in the pipeline 60 for each sensor. This is not viable in practice, but it provides an upper bound on single-sensor performance. The second algorithm fuses the posterior probabilities across the sensors, i.e., the error that results after the sensor fusion 96 of the pipeline 60, without weighting them by the quality index. The third algorithm is essentially the full signal processing pipeline 60, i.e., with weighting of the data based on the signal quality index 98, as discussed above.

Figure 22:
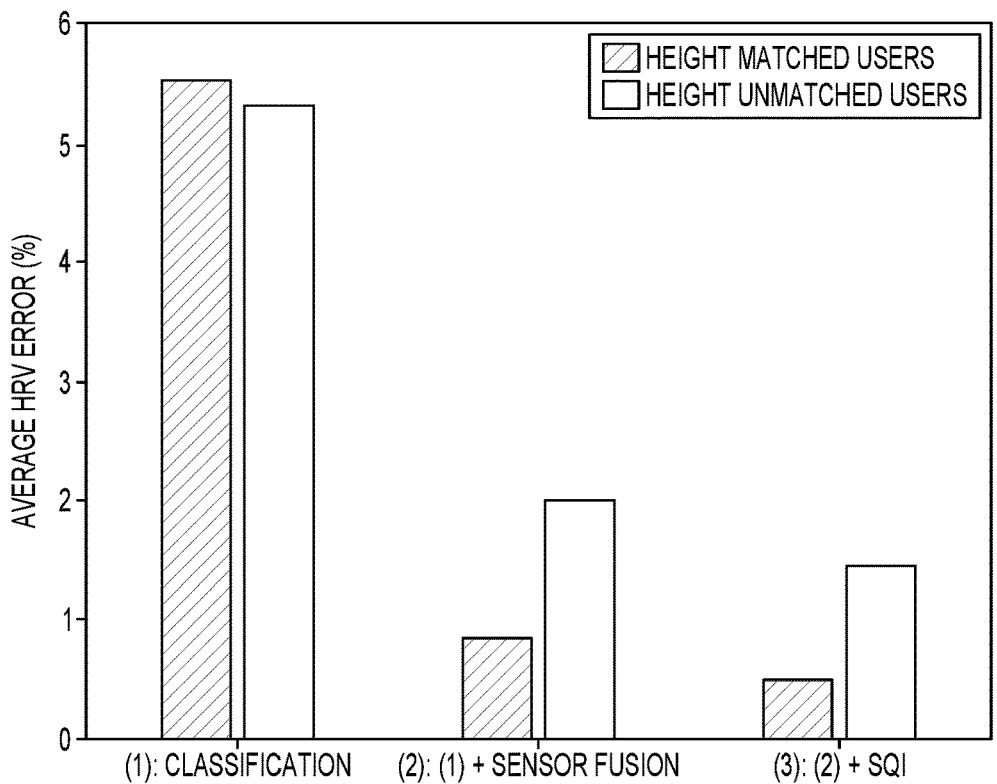
FIG. 22 is a bar graph showing the contribution to the average heart rate variability (HRV) error for different blocks of the example signal processing pipeline of FIG. 8.
Figure 23:
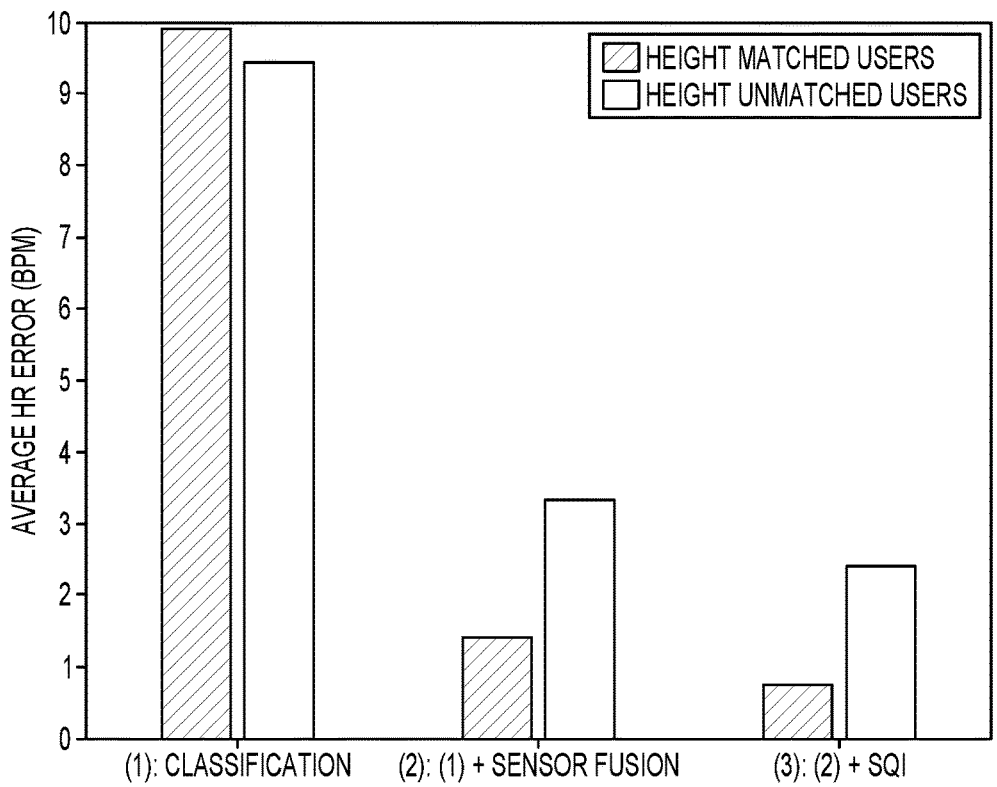
FIG. 23 is a bar graph showing the contribution to the average heart rate error for different blocks of the example signal processing pipeline of FIG. 8.

FIGS. 22 and 23 show the error results for each of these algorithms: i.e., (1) the error after the classification 90 but before the sensor fusion 96 (labeled as "(1): CLASSIFICATION" in FIGS. 22 and 23); (2) the error after the probabilities have been fused 96 across all the sensors without weighting with the signal quality index 98 (labeled as "(2): (1)+SENSOR FUSION" in FIGS. 22 and 23); and (3) the error after weighting the data using the signal quality index 98 (labeled as "(3): (2)+SQI" in FIGS. 22 and 23).

FIG. 22 shows the error contribution to the average heart rate variability (HRV) and FIG. 23 shows the error contribution to the average heart rate. FIGS. 22 and 23 demonstrate that the sensor fusion 96 greatly reduces the system error, with about a six times (6×) reduction for the height-matched participants and about a two and a half times (2.5×) reduction for the height-unmatched participants. The use of a weighted measure using the SQI 98 improves results further, e.g., about two times (2×) for the height-matched participants and about 25% for the height-unmatched participants. As is further shown in FIGS. 22 and 23, the sensor fusion 96 and the SQI weighting 98 in the signal processing pipeline 60 are generally more effective for the height-matched participants than for the height-unmatched participants. This is intuitive since the garment system 10 provides signals from multiple sensors 14, 16 for the height-matched participants such that the sensor fusion 96 works better. However, the results are not much worse for the height-unmatched participants, such that even if the wearer chooses to have an oversized garment shirt 12, the garment system 10 should be able to measure physiological parameters with reasonable accuracy.

These results show the benefits of having a distributed array of sensors 14, 16 on the garment system 10. Unlike earlier wearables like smartwatches that can measure essentially only at a single point on the body, the example garment system 10 has multiple distributed sensors 14, 16, e.g., two sensors in examples where only a single resistive sensor 14 and a single triboelectric sensor 16 is used, up to five or more distributed sensors (i.e., four or more resistive sensors 14 and one or more triboelectric sensors 16 at various positions of the garment 12) whose information is fused such that the garment system 10 described herein can capture a strong signal even if one or two sensors 14, 16 are erroneous due to their positioning.

Individual Resistive Sensor Contribution

Figure 24:
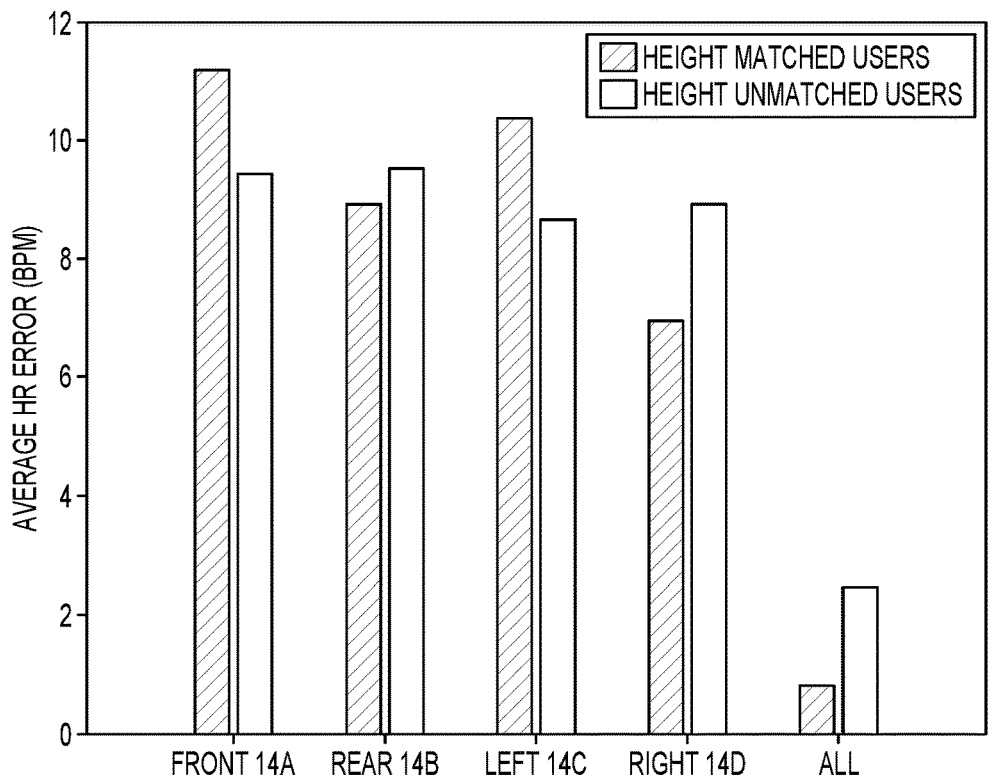
FIG. 24 is a bar graph showing the average heart rate error for each individual sensor of the example garment of FIGS. 2A and 2B compared to the error after fusion in the example signal processing pipeline of FIG. 8.
Figure 25:
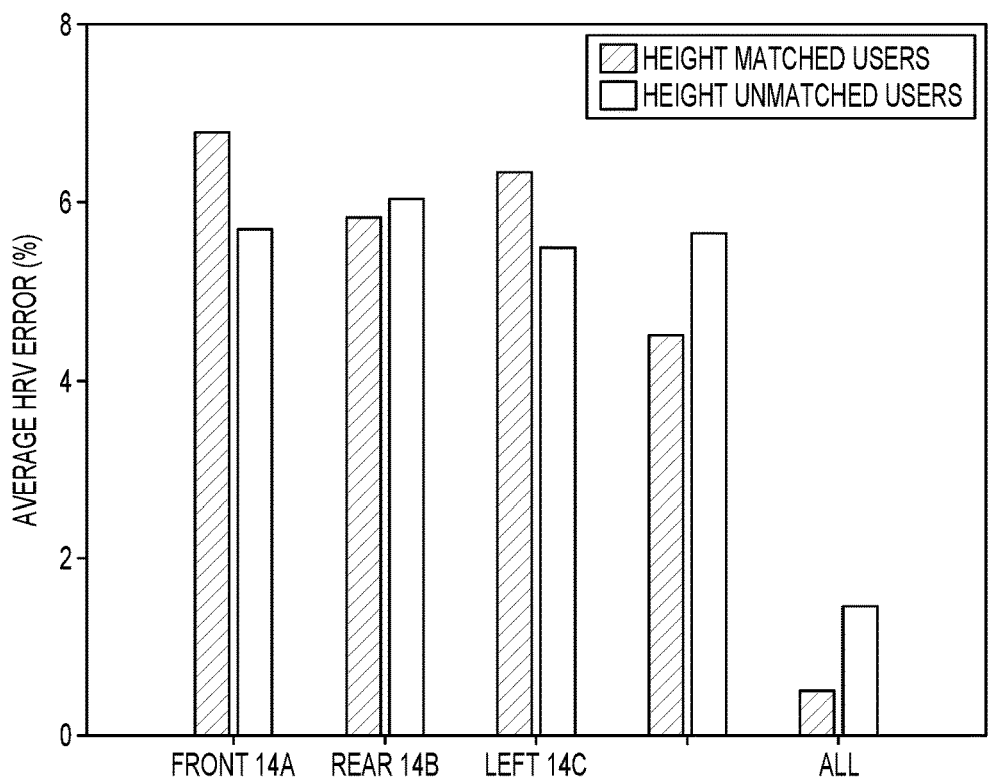
FIG. 25 is a bar graph showing the average heart rate variability (HRV) error for each individual sensor of the example garment of FIGS. 2A and 2B compared to the error after fusion in the example signal processing pipeline of FIG. 8.

Next, the contribution of each resistive sensor 14 to the overall results of the garment system 10 and whether there are specific sensors 14 that are superior to others in terms of determining physiological parameters was investigated. FIGS. 24 and 25 are plots of the accuracy of the garment system 10 if only one resistive sensor 14 (i.e., only front sensor 14A, only rear sensor 14B, only left sensor 14C, and only right sensor 14D) was used and contrast this with the overall accuracy when the information from all of the sensors 14A, 14B, 14C, and 14D are fused together. FIG. 24 shows the error values for average heart rate error, and FIG. 25 shows the error values for the average HRV error.

As can be seen in FIGS. 24 and 25, each resistive sensor 14A, 14B, 14C, and 14D has high error in its own estimate of heart rate and HRV. However, after the sensor fusion 96, the estimation error drops by about 400% to about 500%. This result also highlights the benefits of the sensor fusion 96 and shows that any one resistive sensor 14 is not expected to do as well as fusing readings from multiple sensors 14.

Triboelectric Sensor Contribution

Figure 26:
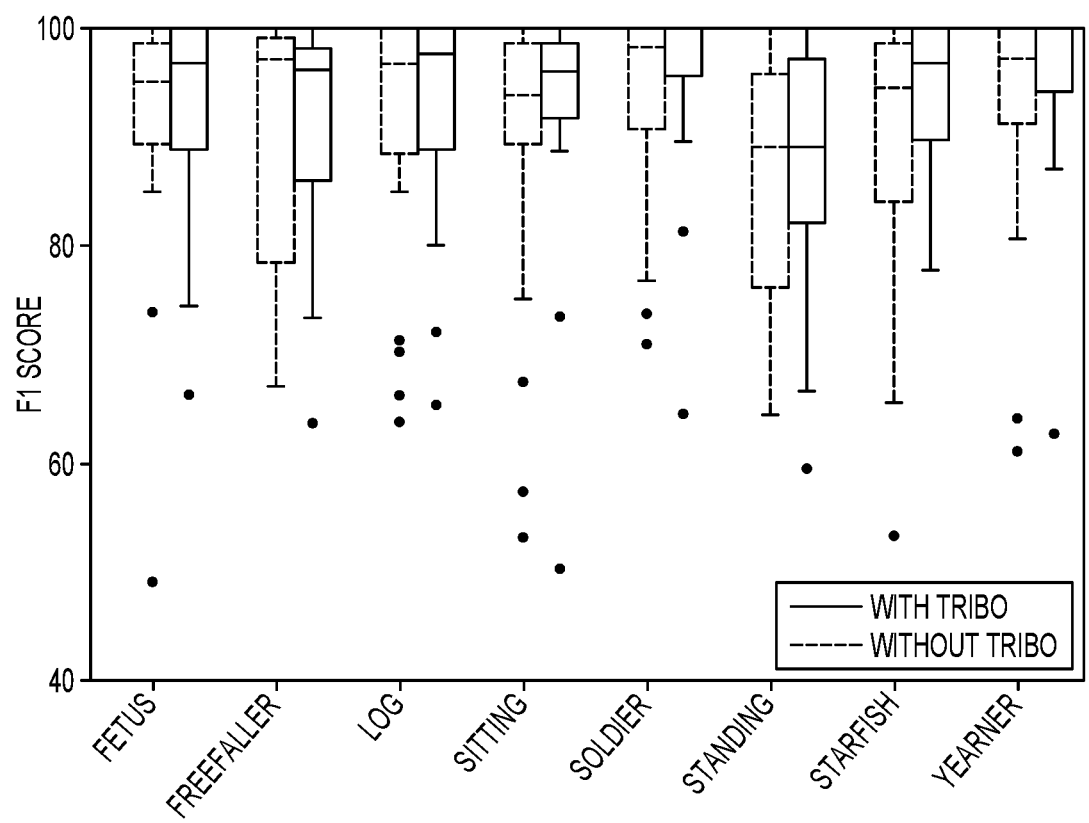
FIG. 26 is a graph of the $F_1$ scores for data measured with the example garment of FIGS. 2A and 2B taken with the triboelectric sensor of FIG. 6 activated and with the triboelectric sensor deactivated.

The contribution of the triboelectric sensor 16 to the overall classification performance was also investigated by comparing the accuracy of the garment system 10 after data fusion 96 of only the resistive sensors 14 are used (i.e., without data from the triboelectric sensor 16) with that of the garment system 10 after data fusion 96 of all of the sensors 14, 16 are used (i.e., with data from all of the resistive sensors 14 and the triboelectric sensor 16). FIG. 26 is bar graph of the $F_1$ scores for all of the postures (i.e., standing, sitting (FIG. 1B), standing (FIG. 1C), and yearner 114, freefaller 116, starfish 118, soldier 120, fetal 122, and log 124 from FIGS. 15A-15F) both with and without data from the triboelectric sensor 16. As can be seen by FIG. 26, inclusion of the envelope features from the triboelectric sensor 16 is informative and improves overall performance by improving the median $F_1$ score and reducing the number of outlier data points.

Subjective Factors

Each participant was asked to complete a survey regarding several subjective aspects of the example garment system 10. First, each participant was asked to rate the comfort of the example garment system on a subjective scale of 1-5 (with 1 being very uncomfortable and 5 being very comfortable). The average subjective comfort rating amongst the 21 participants was 4.95.

Next, each participant was asked if they would be generally interested in tracking vital signs (e.g., heart rate, respiration rate, and HRV) during sleep to determine the general inclination toward logging vital signs during sleep. Seventeen (17) of the participants, or about 81%, reported that they would be interested in tracking vital signs during sleep. Four (4) participants, or about 19%, said that they generally would not be interested.

Third, each participant was asked if they would prefer using the example garment system 10 or a wrist-worn fitness band (e.g., a FITBIT) to track vital signs during sleep. Sixteen (16) participants, or about 76%, reported that they would prefer the example garment system 10 to a wrist-worn fitness tracker for tracking vital signs during sleep. Five (5) participants, or about 24%, said they would prefer the wrist-worn fitness tracker.

Finally, each participant was asked if the example garment system 10 interrupted respiration or impacted their respiration pattern. All twenty-one (21) participants reported that the example garment system 10 did not interfere with breathing at all.

The data of the participants' subjective impressions show that at least this group of participants found the example garment system 10 to be comfortable and unobtrusive. A sizable percentage of the participants also indicated they would prefer the comfort of the example garment system 10 to a wrist-worn fitness tracker like a FITBIT. The inventors believe that a major advantage of the example garment system 10 described herein is the comfortable and unobtrusive nature of its design. The sensors 14, 16 can be integrated into everyday nightwear with discrete elements placed in expected locations like a button. In addition, users do not need to remember to wear an additional device that would be unusual during sleep, like a fitness band.

Although the present disclosure describes the garment system 10 as being used for measurement of vital signs, such as for sleep tracking and evaluation, those of skill in the art will appreciate that the garment system 10 and methods described herein are not limited to sleep. Rather, the example garment system 10 and methods described herein may be usable for fitness applications, such as heart rate and respiration monitoring during exercise. Moreover, the example garment systems and methods described herein are not limited to health applications like sleep and fitness tracking. The example garment system 10 and methods described herein may be used in other contexts, such as to provide sensors for integration into a virtual reality (VR) system, such as to assist in the generation of VR haptics.

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A textile-based garment system comprising:
   a garment substrate formed from one or more textile-based sheets;
   an array of one or more resistive pressure sensors coupled to the garment substrate, wherein each of the one or more resistive pressure sensors comprises;
      a pair of first textile-based outer layers each having an electrical resistance of no more than 100 ohms, and
      a textile-based inner layer sandwiched between the pair of first textile-based outer layers, wherein the textile-based inner layer comprises a textile substrate with a functionalized coating comprising an ion-conductive material including one or more counterions deposited on the textile substrate, wherein the one or more counterions act as an ionic conductor through the textile-based inner layer, wherein a surface resistivity of the functionalized coating is proportional to a surface concentration of the one or more counterions on the ion-conductive material, and wherein the surface concentration changes in response to a pressure being applied to the resistive pressure sensor so that an overall resistivity of the textile-based inner layer is proportional to the pressure being applied to the resistive pressure sensor; and
   electronics configured to process signals from the array of one or more resistive pressure sensors to determine a pressure applied on each of the one or more resistive pressure sensors and to determine one or more physiological properties of a wearer of the garment substrate based on the measured pressures for the one or more resistive pressure sensors.

2. The textile-based garment system of claim 1, wherein the ion-conductive material modifies surface resistivity of the textile-based inner layer compared to a comparable textile substrate without the functionalized coating deposited thereon.

3. The textile-based garment system of claim 2, wherein the functionalized coating has an electrical resistance of from about 0.1 ohms per square inch to about 10,000 ohms per square inch.

4. The textile-based garment system of claim 1, wherein the one or more counterions comprise at least one of: chloride counterions, bromide counterions, iodide counterions, sulfate counterions, acetate counterions, formate counterions, lactate counterions, or combinations thereof.

5. The textile-based garment system of claim 1, wherein the ion-conductive material comprises at least one of: a siloxane containing one or more quaternary ammonium moieties, or a p-doped poly(3,4-ethylenedioxythiophene).

6. The textile-based garment system of claim 5, wherein the p-doped poly(3,4-ethylenedioxythiophene) has the formula:

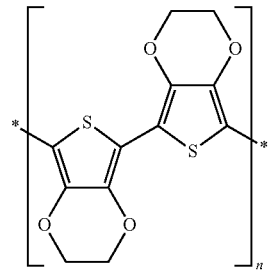

where n is the number of repeat units.

7. The textile-based garment system of claim 1, wherein the ion-conductive material comprises N-trimethoxysilylpropyl-N,N,N,-trimethylammonium chloride.

8. The textile-based garment system of claim 1, further comprising a protective coating layer comprising a hydrophobic material.

9. The textile-based garment system of claim 8, wherein the hydrophobic material comprises a perfluorinated siloxane.

10. The textile-based garment system of claim 1, wherein the one or more physiological properties of the wearer includes one or more of: one or more cardiac properties of the wearer, one or more respiratory properties of the wearer, and one or more posture properties of the wearer.

11. A resistive pressure sensor comprising:
   a pair of textile-based outer layers each having an electrical resistance of no more than 100 ohms; and
   a textile-based inner layer sandwiched between the pair of textile-based outer layers, wherein the textile-based inner layer comprises a textile substrate with a functionalized coating comprising an ion-conductive material including one or more counterions deposited on the textile substrate, wherein the one or more counterions act as an ionic conductor through the textile-based inner layer, wherein a surface resistivity of the functionalized coating is proportional to a surface concentration of the one or more counterions on the ion-conductive material, and wherein the surface concentration changes in response to a pressure being applied to the resistive pressure sensor so that an overall resistivity of the textile-based inner layer is proportional to the pressure being applied to the resistive pressure sensor.

12. The resistive pressure sensor of claim 11, wherein the ion-conductive material modifies surface resistivity of the textile-based inner layer compared to a comparable textile substrate without the functionalized coating deposited thereon.

13. The resistive pressure sensor of claim 11, wherein the functionalized coating has an electrical resistance of from about 0.1 ohms per square inch to about 10,000 ohms per square inch.

14. The resistive pressure sensor of claim 11, wherein the one or more counterions comprise at least one of: chloride counterions, bromide counterions, iodide counterions, sulfate counterions, acetate counterions, formate counterions, lactate counterions, or combinations thereof.

15. The resistive pressure sensor of claim 11, wherein the ion-conductive material comprises at least one of: a siloxane containing one or more quaternary ammonium moieties, or a p-doped poly(3,4-ethylenedioxythiophene).

16. The resistive pressure sensor of claim 15, wherein the p-doped poly(3,4-ethylenedioxythiophene) has the formula:

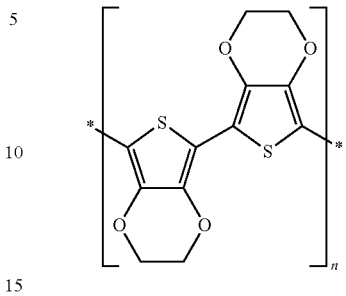

where n is the number of repeat units.

17. The resistive pressure sensor of claim 11, wherein the ion-conductive material comprises N-trimethoxysilylpropyl-N,N,N,-trimethylammonium chloride.

18. The textile-based garment system of claim 1, wherein the textile-based inner layer has an electrical resistance of at least 1 mega-ohm.

19. The resistive pressure sensor of claim 11, wherein the textile-based inner layer has an electrical resistance of at least 1 mega-ohm.

* * * * *